(12) United States Patent
O'Connor et al.

(10) Patent No.: US 11,774,427 B2
(45) Date of Patent: Oct. 3, 2023

(54) METHODS AND APPARATUS FOR MONITORING HEALTH OF FUEL OXYGEN CONVERSION UNIT

(71) Applicant: General Electric Company, Schenectady, NY (US)

(72) Inventors: Ethan Patrick O'Connor, Hamilton, OH (US); Nathan Ray Parrott, Sunman, IN (US)

(73) Assignee: General Electric Company, Schenectady, NY (US)

(*) Notice: Subject to any disclaimer, the term of this patent is extended or adjusted under 35 U.S.C. 154(b) by 337 days.

(21) Appl. No.: 16/697,257

(22) Filed: Nov. 27, 2019

(65) Prior Publication Data
US 2021/0156291 A1   May 27, 2021

(51) Int. Cl.
| | | |
|---|---|---|
| G01N 33/00 | (2006.01) | |
| F01N 11/00 | (2006.01) | |
| F02D 41/14 | (2006.01) | |
| H01M 8/04089 | (2016.01) | |
| B01D 19/00 | (2006.01) | |

(52) U.S. Cl.
CPC ..... *G01N 33/0063* (2013.01); *B01D 19/0005* (2013.01); *F01N 11/007* (2013.01); *F02D 41/1454* (2013.01); *F02D 41/1495* (2013.01); *H01M 8/04097* (2013.01)

(58) Field of Classification Search
None
See application file for complete search history.

(56) References Cited

U.S. PATENT DOCUMENTS

| | | | |
|---|---|---|---|
| 2,582,842 A | 1/1952 | Messinger | |
| 2,720,313 A | 10/1955 | Pattison | |
| 2,893,628 A | 7/1959 | Herman | |
| 3,050,240 A | 8/1962 | Darnell | |

(Continued)

FOREIGN PATENT DOCUMENTS

| | | | |
|---|---|---|---|
| CN | 108037251 | | 5/2018 |
| EP | 0536271 B1 | | 4/1994 |

(Continued)

OTHER PUBLICATIONS

U.S. Appl. No. 16/179,124, filed Nov. 28, 2018.

(Continued)

*Primary Examiner* — Christopher P Jones
*Assistant Examiner* — Phillip Y Shao
(74) *Attorney, Agent, or Firm* — Dority & Manning, P.A.

(57) ABSTRACT

Methods of and apparatus for monitoring the health of a fuel oxygen conversion unit for a vehicle or a vehicle engine are provided. For example, a method comprises providing a distribution of sensed values obtained from a plurality of sensors distributed along an axial length of a gas oxygen reduction unit of the fuel oxygen conversion unit and determining the health of the fuel oxygen conversion unit from the distribution. As another example, a fuel oxygen conversion unit defines a circulation gas flowpath from a fuel gas separator to a contactor and comprises a gas oxygen reduction unit positioned in the circulation gas flowpath for reducing an oxygen content of a flow of stripping gas through the circulation gas flowpath. A plurality of sensors are distributed along an axial length of the gas oxygen reduction unit.

14 Claims, 6 Drawing Sheets

(56) References Cited

U.S. PATENT DOCUMENTS

| | | | |
|---|---|---|---|
| 3,178,105 | A | 4/1965 | Darnell |
| 3,590,559 | A | 7/1971 | Bragg |
| 3,847,298 | A | 11/1974 | Hamilton |
| 3,895,243 | A | 7/1975 | Amend et al. |
| 3,902,658 | A | 9/1975 | Madsen |
| 4,169,567 | A | 10/1979 | Tamura |
| 4,170,116 | A | 10/1979 | Williams |
| 4,449,372 | A | 5/1984 | Rilett |
| 4,503,682 | A | 3/1985 | Rosenblatt |
| 4,505,124 | A | 3/1985 | Mayer |
| 4,550,573 | A | 11/1985 | Rannenberg |
| 4,600,413 | A | 7/1986 | Sugden |
| 4,705,100 | A | 11/1987 | Black et al. |
| 4,714,139 | A | 12/1987 | Lorenz et al. |
| 4,738,779 | A | 4/1988 | Carroll et al. |
| 4,755,197 | A | 7/1988 | Benson et al. |
| 4,773,212 | A | 9/1988 | Griffin et al. |
| 5,149,018 | A | 9/1992 | Clark |
| 5,267,608 | A | 12/1993 | Coffinberry |
| 5,320,518 | A | 6/1994 | Stilger et al. |
| 5,341,636 | A | 8/1994 | Paul |
| 5,452,573 | A | 9/1995 | Glickstein et al. |
| 5,587,068 | A | 12/1996 | Aho, Jr. et al. |
| 5,622,621 | A | 4/1997 | Kramer |
| 5,667,168 | A | 9/1997 | Fluegel |
| 5,722,241 | A | 3/1998 | Huber |
| 5,724,806 | A | 3/1998 | Homer |
| 5,904,836 | A | 5/1999 | Lee et al. |
| 6,134,876 | A | 10/2000 | Hines et al. |
| 6,182,435 | B1 | 2/2001 | Niggemann et al. |
| 6,250,097 | B1 | 6/2001 | Lui et al. |
| 6,294,091 | B1 | 9/2001 | Hoff |
| 6,315,815 | B1* | 11/2001 | Spadaccini ............ B01D 61/00 96/6 |
| 6,415,595 | B1 | 7/2002 | Wilmot, Jr. et al. |
| 6,435,454 | B1 | 8/2002 | Engelhardt |
| 6,701,717 | B2 | 3/2004 | Flatman et al. |
| 6,702,729 | B2 | 3/2004 | Mazzuca |
| 6,892,710 | B2 | 5/2005 | Ekstam |
| 6,939,392 | B2 | 9/2005 | Huang et al. |
| 7,093,437 | B2 | 8/2006 | Spadaccini et al. |
| 7,260,926 | B2 | 8/2007 | Sabatino et al. |
| 7,334,407 | B2 | 2/2008 | Spadaccini et al. |
| 7,377,098 | B2 | 5/2008 | Walker et al. |
| 7,387,602 | B1 | 6/2008 | Kirsch |
| 7,398,641 | B2 | 7/2008 | Stretton et al. |
| 7,431,818 | B2 | 10/2008 | Cipollini |
| 7,459,081 | B2 | 12/2008 | Koenig et al. |
| 7,536,851 | B2 | 5/2009 | McLain |
| 7,537,646 | B2* | 5/2009 | Chen ...................... F02C 7/224 95/8 |
| 7,569,099 | B2 | 8/2009 | Coffin et al. |
| 7,628,965 | B2* | 12/2009 | Johnson ................. C01B 32/50 96/108 |
| 7,694,916 | B2 | 4/2010 | Limaye et al. |
| 7,735,670 | B2* | 6/2010 | Zaki ...................... B64D 37/32 244/135 R |
| 7,744,827 | B2 | 6/2010 | Vanderspurt et al. |
| 7,824,470 | B2 | 11/2010 | Chiappetta et al. |
| 7,836,680 | B2 | 11/2010 | Schwarz et al. |
| 7,882,704 | B2 | 2/2011 | Chen |
| 7,896,292 | B2 | 3/2011 | Limaye et al. |
| 7,905,259 | B2 | 3/2011 | Johnson et al. |
| 7,966,807 | B2 | 6/2011 | Norris et al. |
| 7,987,676 | B2 | 8/2011 | Ast et al. |
| 8,055,437 | B2 | 11/2011 | Proietty et al. |
| 8,141,360 | B1 | 3/2012 | Huber |
| 8,177,884 | B2 | 5/2012 | Schmidt et al. |
| 8,231,714 | B2 | 7/2012 | Cornet et al. |
| 8,261,528 | B2 | 9/2012 | Chillar et al. |
| 8,327,618 | B2* | 12/2012 | Endo ...................... F01N 3/101 60/277 |
| 8,388,830 | B2 | 3/2013 | Sohn et al. |
| 8,449,656 | B2* | 5/2013 | Wu ........................ C02F 1/20 96/201 |
| 8,450,020 | B2 | 5/2013 | Sinha et al. |
| 8,499,567 | B2 | 8/2013 | Hagh et al. |
| 8,499,822 | B2 | 8/2013 | Bulin et al. |
| 8,522,572 | B2 | 9/2013 | Coffinberry et al. |
| 8,602,362 | B2 | 12/2013 | Buchwald |
| 8,663,996 | B2* | 3/2014 | Beeson ................. B64D 37/32 422/111 |
| 8,765,070 | B2 | 7/2014 | Norton et al. |
| 8,789,377 | B1 | 7/2014 | Brostmeyer |
| 8,821,362 | B2 | 9/2014 | Kidd et al. |
| 8,828,344 | B2 | 9/2014 | K-WLam et al. |
| 8,858,161 | B1 | 10/2014 | Ryznic et al. |
| 8,944,367 | B2 | 2/2015 | Bystry, Jr. et al. |
| 8,978,353 | B2 | 3/2015 | Norton et al. |
| 8,984,884 | B2 | 3/2015 | Xu et al. |
| 9,014,791 | B2 | 4/2015 | Held |
| 9,038,397 | B2 | 5/2015 | Papa et al. |
| 9,120,580 | B2* | 9/2015 | Sampath ............ B01D 19/0031 |
| 9,144,768 | B2 | 9/2015 | Tichborne et al. |
| 9,162,162 | B2 | 10/2015 | Yount |
| 9,231,267 | B2 | 1/2016 | McAlister |
| 9,435,246 | B2* | 9/2016 | Devarakonda ........ F01N 11/007 |
| 9,567,095 | B2 | 2/2017 | McCarthy et al. |
| 9,580,185 | B2 | 2/2017 | Rhoden et al. |
| 9,656,187 | B2 | 5/2017 | Lo et al. |
| 9,678,029 | B2 | 6/2017 | Rateick |
| 9,687,773 | B2 | 6/2017 | Johnson et al. |
| 9,724,625 | B2 | 8/2017 | Lo |
| 9,752,458 | B2 | 9/2017 | Huntington et al. |
| 9,752,507 | B2 | 9/2017 | Selstad et al. |
| 9,771,867 | B2 | 9/2017 | Karam et al. |
| 9,834,315 | B2 | 12/2017 | Lo et al. |
| 9,863,322 | B2 | 1/2018 | Williams et al. |
| 9,885,290 | B2 | 2/2018 | Della-Fera et al. |
| 9,897,054 | B2 | 2/2018 | Lo et al. |
| 9,925,497 | B2 | 3/2018 | Daniello |
| 11,187,156 | B2 | 11/2021 | Niergarth et al. |
| 2003/0221415 | A1* | 12/2003 | Rosel .................... F01N 11/007 60/285 |
| 2007/0006591 | A1* | 1/2007 | Spadaccini ............ B01B 1/005 60/734 |
| 2007/0220863 | A1* | 9/2007 | Iida ...................... F01N 13/009 60/285 |
| 2009/0133380 | A1 | 5/2009 | Donnerhack |
| 2009/0158739 | A1 | 6/2009 | Messmer |
| 2009/0188234 | A1 | 7/2009 | Suciu et al. |
| 2010/0212857 | A1 | 8/2010 | Bulin et al. |
| 2010/0313591 | A1 | 12/2010 | Lents et al. |
| 2011/0072790 | A1* | 3/2011 | Schmieg ............ F02D 41/1445 60/299 |
| 2011/0262309 | A1 | 10/2011 | Limaye et al. |
| 2012/0216502 | A1 | 8/2012 | Freund et al. |
| 2012/0216677 | A1 | 8/2012 | Koenig et al. |
| 2013/0186100 | A1 | 7/2013 | Rhoden et al. |
| 2014/0165570 | A1 | 6/2014 | Herring |
| 2014/0205446 | A1 | 7/2014 | Patsouris et al. |
| 2014/0345292 | A1 | 11/2014 | Diaz et al. |
| 2014/0360153 | A1 | 12/2014 | Papa et al. |
| 2015/0000291 | A1 | 1/2015 | Smith et al. |
| 2015/0040986 | A1 | 2/2015 | Tichborne et al. |
| 2015/0072850 | A1 | 3/2015 | Derrick et al. |
| 2015/0159867 | A1 | 6/2015 | Patrick et al. |
| 2015/0314229 | A1* | 11/2015 | Johnson ............ B01D 19/0026 422/187 |
| 2016/0003160 | A1 | 1/2016 | Hagshenas |
| 2016/0096629 | A1 | 4/2016 | Vaisman |
| 2016/0108814 | A1 | 4/2016 | Schmitz |
| 2016/0138431 | A1 | 5/2016 | Lear, Jr. |
| 2016/0167802 | A1* | 6/2016 | Lo ........................ B64D 37/34 96/187 |
| 2016/0208759 | A1 | 7/2016 | Lo et al. |
| 2016/0245144 | A1* | 8/2016 | Selberg ............... F02D 41/2435 |
| 2016/0290214 | A1 | 10/2016 | Ekanayake et al. |
| 2016/0305440 | A1* | 10/2016 | Laboda ................ B01D 45/14 |
| 2016/0356224 | A1* | 12/2016 | Farnum ................ F02C 7/30 |
| 2016/0369700 | A1 | 12/2016 | Ribarov et al. |

(56) References Cited

U.S. PATENT DOCUMENTS

| | | | |
|---|---|---|---|
| 2017/0014774 A1* | 1/2017 | Daniello | B01D 63/02 |
| 2017/0030266 A1 | 2/2017 | Cemy et al. | |
| 2017/0096910 A1 | 4/2017 | Raimarckers et al. | |
| 2017/0113807 A1* | 4/2017 | Burnell | B64D 37/28 |
| 2017/0114721 A1 | 4/2017 | Miller et al. | |
| 2017/0138922 A1* | 5/2017 | Potyrailo | G01M 13/021 |
| 2017/0141419 A1 | 5/2017 | Wu et al. | |
| 2017/0159566 A1 | 6/2017 | Sennoun et al. | |
| 2017/0167382 A1 | 6/2017 | Miller et al. | |
| 2017/0227425 A1* | 8/2017 | Martucci | G01N 33/22 |
| 2017/0291714 A1 | 10/2017 | Corman | |
| 2018/0016025 A1* | 1/2018 | Rheaume | B64D 37/34 |
| 2018/0056233 A1 | 3/2018 | Henson et al. | |
| 2018/0056234 A1 | 3/2018 | Weng et al. | |
| 2018/0071659 A1 | 3/2018 | Rhoden | |
| 2018/0118367 A1 | 5/2018 | Rheaume et al. | |
| 2018/0179940 A1 | 6/2018 | Hall et al. | |
| 2019/0153952 A1 | 5/2019 | Niergarth et al. | |
| 2019/0153953 A1 | 5/2019 | Niergarth et al. | |
| 2019/0177000 A1 | 6/2019 | Manoukian et al. | |

FOREIGN PATENT DOCUMENTS

| | | |
|---|---|---|
| EP | 2003311 A2 | 12/2008 |
| EP | 3018304 A1 | 5/2016 |
| EP | 3075957 A1 | 10/2016 |
| GB | 2136880 A | 9/1984 |
| GB | 2204361 A | 11/1988 |
| JP | S5932893 U | 2/1984 |
| WO | WO9200519 A1 | 1/1992 |
| WO | WO02/16743 A1 | 2/2002 |
| WO | WO2002/038938 A1 | 5/2002 |
| WO | WO2006/079438 A1 | 8/2006 |
| WO | WO2011/038188 A1 | 3/2011 |

OTHER PUBLICATIONS

Kelburn Engineering, Landfill, Sewage, Biogas, Coal, Seam & Mines Gas Separation/Filtration, LandfillGas and Air Separation, 3 pages, date: Feb. 21, 2018 www.kelburneng.com.us/landfill-gas-bio-gas-sewer-gas.php.

* cited by examiner

METHODS AND APPARATUS FOR MONITORING HEALTH OF FUEL OXYGEN CONVERSION UNIT

FIELD

The present subject matter relates generally to a fuel oxygen conversion unit for an engine and a method of operating the same, as well as to methods and apparatus for monitoring the health of the fuel oxygen conversion unit.

BACKGROUND

Typical aircraft propulsion systems include one or more gas turbine engines. The gas turbine engines generally include a turbomachine, the turbomachine including, in serial flow order, a compressor section, a combustion section, a turbine section, and an exhaust section. In operation, air is provided to an inlet of the compressor section where one or more axial compressors progressively compress the air until it reaches the combustion section. Fuel is mixed with the compressed air and burned within the combustion section to provide combustion gases. The combustion gases are routed from the combustion section to the turbine section. The flow of combustion gasses through the turbine section drives the turbine section and is then routed through the exhaust section, e.g., to atmosphere.

Certain operations and systems of the gas turbine engines and aircraft may generate a relatively large amount of heat. Fuel has been determined to be an efficient heat sink to receive at least some of such heat during operations due at least in part to its heat capacity and an increased efficiency in combustion operations that may result from combusting higher temperature fuel.

However, heating the fuel up without properly conditioning the fuel may cause the fuel to "coke," or form solid particles that may clog up certain components of the fuel system, such as the fuel nozzles. Reducing an amount of oxygen in the fuel may effectively reduce the likelihood that the fuel will coke beyond an unacceptable amount. Fuel oxygen conversion systems have been proposed for such a purpose. Certain of these fuel oxygen conversion systems may introduce a stripping gas to absorb or otherwise react with the fuel to reduce an oxygen content of the fuel. Likewise, the oxygen may be removed from the stripping gas such that the stripping gas may be reused within the system. However, if not properly removed, excess oxygen in the stripping gas can reduce the performance of the fuel oxygen conversion system, which cause undesirable results, such as fouling of the combustion system, if sufficient oxygen is not removed from the fuel.

Accordingly, methods and apparatus for monitoring the health of a fuel oxygen conversion unit to determine whether sufficient oxygen is being removed from the fuel would be useful.

BRIEF DESCRIPTION

Aspects and advantages of the invention will be set forth in part in the following description, or may be obvious from the description, or may be learned through practice of the invention.

In one exemplary embodiment of the present disclosure, a method of monitoring the health of a fuel oxygen conversion unit for a vehicle or an engine of the vehicle is provided. The method comprises providing a distribution of sensed values obtained from a plurality of sensors distributed along an axial length of a gas oxygen reduction unit of the fuel oxygen conversion unit and determining the health of the fuel oxygen conversion unit from the distribution.

In another exemplary embodiment of the present disclosure, a fuel oxygen conversion unit for a vehicle or an engine of the vehicle is provided. The fuel oxygen conversion unit comprises a contactor and a fuel gas separator. The fuel oxygen conversion unit defines a circulation gas flowpath from the fuel gas separator to the contactor. The fuel oxygen conversion unit further comprises a gas oxygen reduction unit positioned in the circulation gas flowpath for reducing an oxygen content of a flow of stripping gas through the circulation gas flowpath. A plurality of sensors are distributed along an axial length of the gas oxygen reduction unit.

In an exemplary aspect of the present disclosure, a method of monitoring the health of a fuel oxygen conversion unit for a vehicle or an engine of the vehicle is provided. The method comprises providing a temperature from each temperature sensor of a plurality of temperature sensors, the plurality of temperature sensors distributed axially along a pre-heater of the fuel oxygen conversion unit, the pre-heater disposed upstream of a gas oxygen reduction unit of the fuel oxygen conversion unit; and determining the health of the fuel oxygen conversion unit using a change in temperature from an inlet to an outlet of the pre-heater.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which.

DETAILED DESCRIPTION

Figure 1:
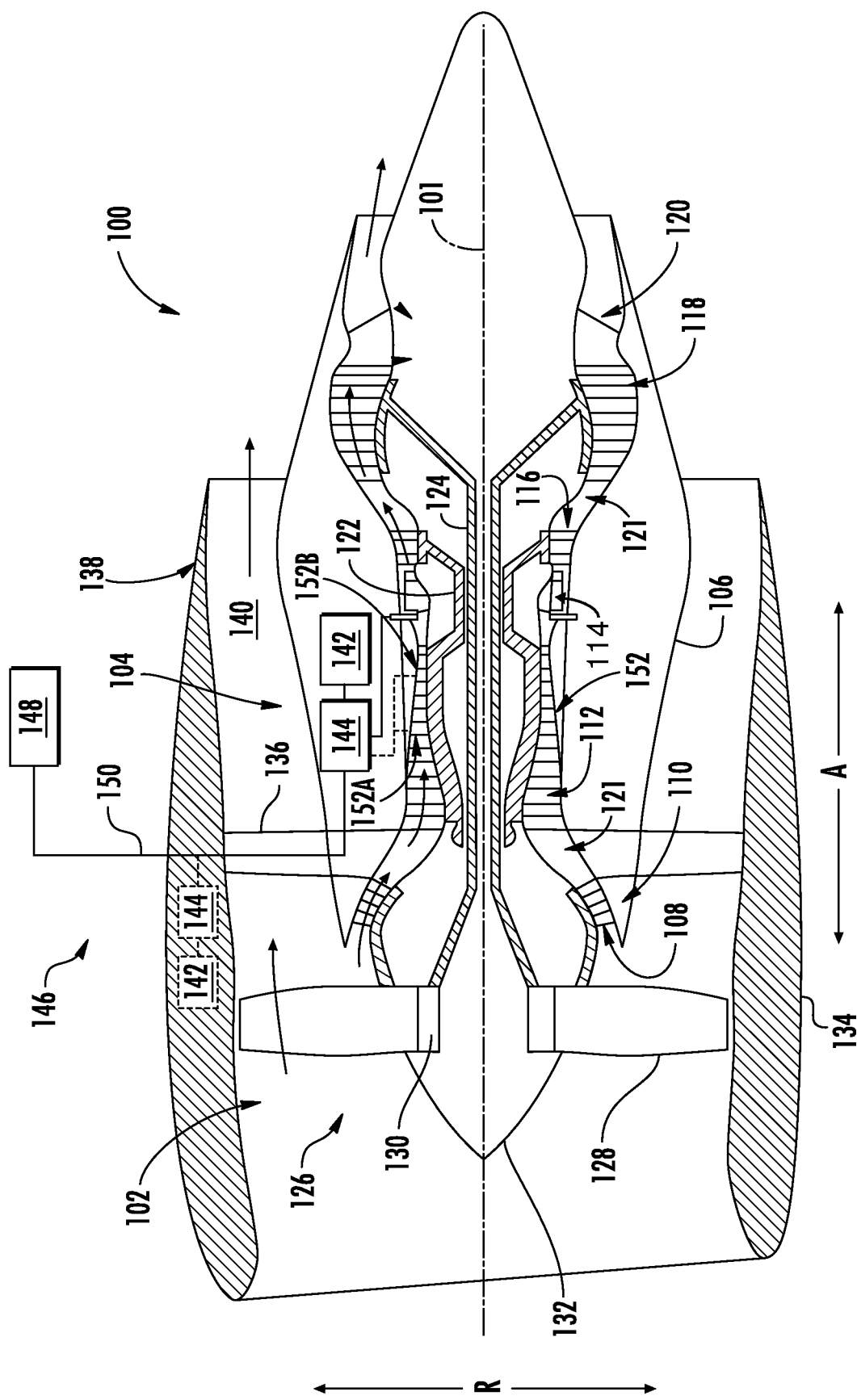
FIG. 1 is a schematic, cross-sectional view of a gas turbine engine in accordance with an exemplary embodiment of the present subject matter.

Reference will now be made in detail to embodiments of the present subject matter, one or more examples of which are illustrated in the accompanying drawings. The detailed description uses numerical and letter designations to refer to features in the drawings. Like or similar designations in the drawings and description have been used to refer to like or similar parts of the present subject matter.

As used herein, the terms "first," "second," and "third" may be used interchangeably to distinguish one component from another and are not intended to signify location or importance of the individual components.

The terms "upstream" and "downstream" refer to the relative direction with respect to fluid flow in a fluid pathway. For example, "upstream" refers to the direction from which the fluid flows and "downstream" refers to the direction to which the fluid flows.

The terms "coupled," "fixed," "attached to," and the like refer to both direct coupling, fixing, or attaching, as well as indirect coupling, fixing, or attaching through one or more intermediate components or features, unless otherwise specified herein.

The singular forms "a," "an," and "the" include plural references unless the context clearly dictates otherwise.

Approximating language, as used herein throughout the specification and claims, is applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value, or the precision of the methods or machines for constructing or manufacturing the components and/or systems. For example, the approximating language may refer to being within a 10 percent margin.

Here and throughout the specification and claims, range limitations are combined and interchanged, such ranges are identified and include all the sub-ranges contained therein unless context or language indicates otherwise. For example, all ranges disclosed herein are inclusive of the endpoints, and the endpoints are independently combinable with each other.

Referring now to the drawings, wherein identical numerals indicate the same elements throughout the figures, FIG. 1 provides a schematic, cross-sectional view of an engine in accordance with an exemplary embodiment of the present disclosure. The engine may be incorporated into a vehicle. For example, the engine may be an aeronautical engine incorporated into an aircraft. Alternatively, however, the engine may be any other suitable type of engine for any other suitable vehicle.

For the embodiment depicted, the engine is configured as a high bypass turbofan engine 100. As shown in FIG. 1, the turbofan engine 100 defines an axial direction A (extending parallel to a longitudinal centerline 101 provided for reference), a radial direction R, and a circumferential direction (extending about the axial direction A; not depicted in FIG. 1). In general, the turbofan 100 includes a fan section 102 and a turbomachine 104 disposed downstream from the fan section 102.

The depicted exemplary turbomachine 104 generally includes a substantially tubular outer casing 106 that defines an annular inlet 108. The outer casing 106 encases, in serial flow relationship, a compressor section including a booster or low pressure (LP) compressor 110 and a high pressure (HP) compressor 112; a combustion section 114; a turbine section including a high pressure (HP) turbine 116 and a low pressure (LP) turbine 118; and a jet exhaust nozzle section 120. The compressor section, combustion section 114, and turbine section together define at least in part a core air flowpath 121 extending from the annular inlet 108 to the jet nozzle exhaust section 120. The turbofan engine further includes one or more drive shafts. More specifically, the turbofan engine includes a high pressure (HP) shaft or spool 122 drivingly connecting the HP turbine 116 to the HP compressor 112, and a low pressure (LP) shaft or spool 124 drivingly connecting the LP turbine 118 to the LP compressor 110.

For the embodiment depicted, the fan section 102 includes a fan 126 having a plurality of fan blades 128 coupled to a disk 130 in a spaced apart manner. The fan blades 128 and disk 130 are together rotatable about the longitudinal axis 101 by the LP shaft 124. The disk 130 is covered by rotatable front hub 132 aerodynamically contoured to promote an airflow through the plurality of fan blades 128. Further, an annular fan casing or outer nacelle 134 is provided, circumferentially surrounding the fan 126 and/or at least a portion of the turbomachine 104. The nacelle 134 is supported relative to the turbomachine 104 by a plurality of circumferentially-spaced outlet guide vanes 136. A downstream section 138 of the nacelle 134 extends over an outer portion of the turbomachine 104 so as to define a bypass airflow passage 140 therebetween.

Referring still to FIG. 1, the turbofan engine 100 additionally includes an accessory gearbox 142 and a fuel delivery system 146 having a fuel oxygen reduction unit 144. For the embodiment shown, the accessory gearbox 142 is located within the cowling/outer casing 106 of the turbomachine 104. Additionally, it will be appreciated that, although not depicted schematically in FIG. 1, the accessory gearbox 142 may be mechanically coupled to, and rotatable with, one or more shafts or spools of the turbomachine 104. For example, in at least certain exemplary embodiments, the accessory gearbox 142 may be mechanically coupled to, and rotatable with, the HP shaft 122. Further, for the embodiment shown, the fuel oxygen reduction unit 144 is coupled to, or otherwise rotatable with, the accessory gearbox 142. In such a manner, it will be appreciated that the exemplary fuel oxygen reduction unit 144 is driven by the accessory gearbox 142. Notably, as used herein, the term "fuel oxygen reduction unit" generally means a device capable of reducing a free oxygen content of the fuel, such as a fuel deoxygenation unit, a fuel oxygen conversion unit, etc.

Briefly, it will it will also be appreciated that the HP compressor 112 of the compressor section of the turbofan engine 100 includes a plurality of stages 152 of compressor rotor blades and compressor stator vanes. Particularly, for the embodiment shown, the HP compressor includes at least four (4) stages 152, such as at least six (6) stages 152, such as up to twenty (20) stages 20, and, more particularly, includes seven (7) stages 152 of compressor rotor blades and compressor stator vanes.

Referring still to FIG. 1, the fuel delivery system 146 generally includes a fuel source 148, such as a fuel tank, and one or more fuel lines 150. The one or more fuel lines 150 provide a fuel flow through the fuel delivery system 146 to the combustion section 114 of the turbomachine 104 of the turbofan engine 100. Notably, for the embodiment shown, the exemplary fuel oxygen reduction unit 144 includes one or more components (such as a makeup gas assembly, as will be discussed in greater detail below) in airflow communication with the HP compressor 112 for receiving an airflow from the HP compressor 112. Particularly, as is depicted in phantom in FIG. 1, the exemplary fuel oxygen reduction unit 144 may be in airflow communication with the HP compressor 112 at the fourth stage 152A, or downstream of the fourth stage 152A, such as at the sixth stage 152B or downstream of the sixth stage 152B.

It will be appreciated, however, that the exemplary turbofan engine 100 depicted in FIG. 1 is provided by way of example only. In other exemplary embodiments, any other suitable engine may be utilized with aspects of the present disclosure. For example, in other embodiments, the engine may be any other suitable gas turbine engine, such as a turboshaft engine, turboprop engine, turbojet engine, etc. In such a manner, it will further be appreciated that in other embodiments the gas turbine engine may have any other suitable configuration, such as any other suitable number or arrangement of shafts, compressors, turbines, fans, etc. Further, although the exemplary gas turbine engine depicted in FIG. 1 is shown schematically as a direct drive, fixed-pitch turbofan engine 100, in other embodiments, a gas turbine engine of the present disclosure may be a geared gas turbine engine (i.e., including a gearbox between the fan 126 and shaft driving the fan, such as the LP shaft 124), may be a variable pitch gas turbine engine (i.e., including a fan 126 having a plurality of fan blades 128 rotatable about their respective pitch axes), etc. Further, although not depicted herein, in other embodiments the gas turbine engine may be any other suitable type of gas turbine engine, such as an industrial gas turbine engine incorporated into a power generation system, a nautical gas turbine engine, etc. Further still, in alternative embodiments, aspects of the present disclosure may be incorporated into, or otherwise utilized with, any other type of engine, such as reciprocating engines. Further, although the exemplary gas turbine engine depicted in FIG. 1 includes a casing 134 surrounding the fan and output guide vanes 136, in other embodiments, a gas turbine engine of the present disclosure may be configured as an open rotor or unducted fan gas turbine engine.

Moreover, it will be appreciated that although for the depicted embodiment the turbofan engine 100 includes the accessory gearbox 142 and fuel oxygen reduction unit 144 positioned within the turbomachine 104, i.e., within the casing 106 of the turbomachine 104, in other embodiments, the accessory gearbox 142 and/or the fuel oxygen reduction unit 144 may be positioned at any other suitable location. For example, as is depicted in phantom in FIG. 1, in other embodiments, the accessory gearbox 142 and/or the fuel oxygen reduction unit 144 may be positioned within the nacelle 134 of the turbofan engine 100. Alternatively, in still other embodiments, the accessory gearbox 142 may be positioned with the turbofan engine 100 and the fuel oxygen reduction unit 144 may be positioned remote from the turbofan engine 100, such as proximate to, or within, the tank 148 of the fuel delivery system 146. Additionally, in other embodiments, the fuel oxygen reduction unit 144 may additionally or alternatively be driven by other suitable power sources such as an electric motor, a hydraulic motor, or an independent mechanical coupling to the HP or LP shaft, etc. For example, when the accessory gearbox 142 is driven by an electric motor, the electric motor may be configured to receive electrical power from an electric machine/generator being driven by the engine, such as an LP or HP system of the engine.

Figure 2:
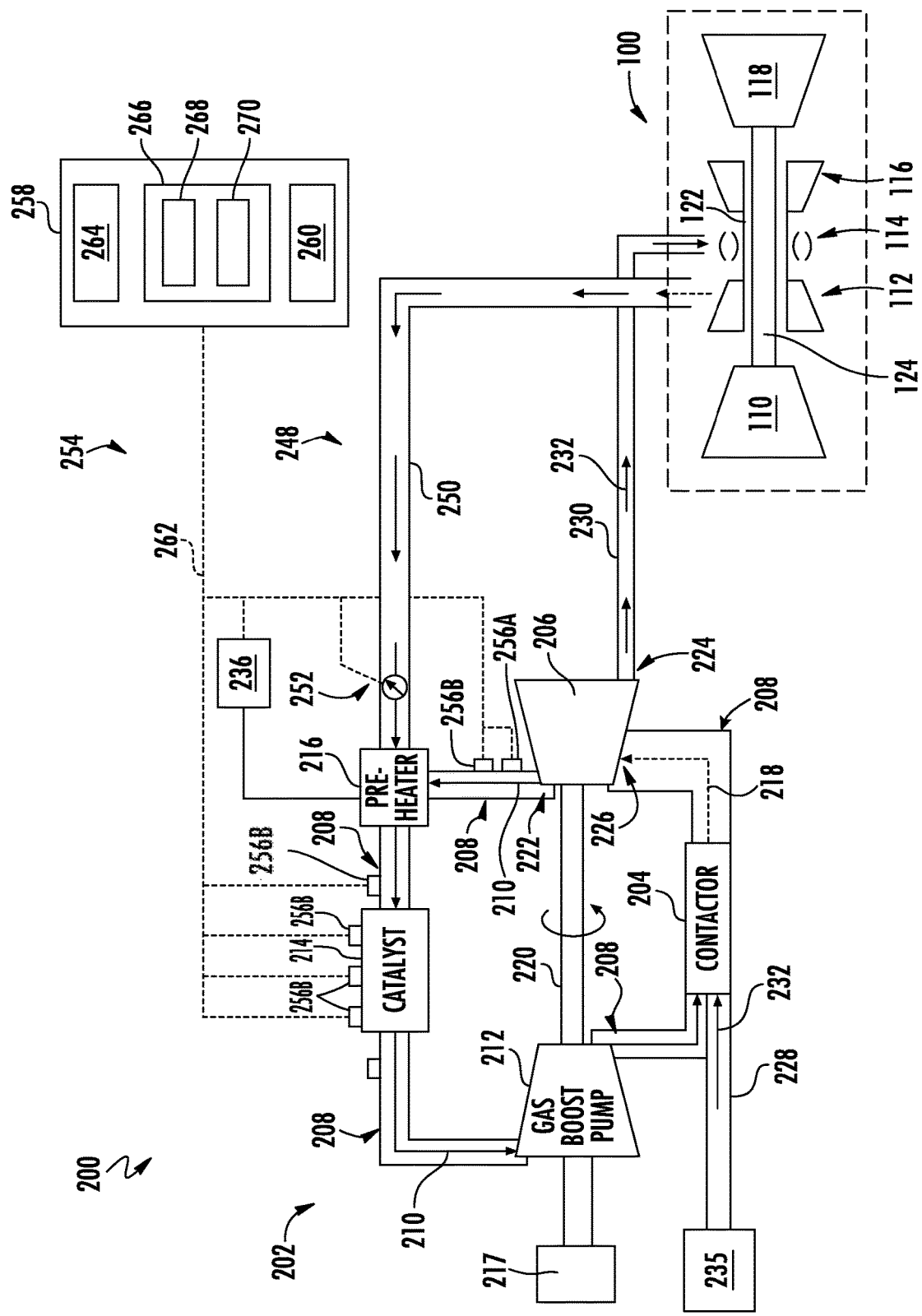
FIG. 2 is a schematic view of a fuel delivery system according to an exemplary embodiment of the present subject matter.

Referring now to FIG. 2, a schematic drawing of a fuel delivery system 200 including a fuel oxygen reduction unit 202 in accordance with an exemplary aspect of the present disclosure is provided. In at least certain exemplary embodiments, the exemplary fuel delivery system 200 depicted in FIG. 2 may be incorporated into, the exemplary turbofan engine 100 described above with reference to FIG. 1 (e.g., may be the fuel delivery system 146 depicted in FIG. 1 and described above). More specifically, the exemplary fuel delivery system 200 of FIG. 2 may be operable with, e.g., included with, an engine 100. For the embodiment depicted in FIG. 2, the engine 100 is depicted schematically and is configured as a gas turbine engine 100. The exemplary gas turbine engine 100 may be configured in a similar manner to the exemplary turbofan engine 100 described above with reference to FIG. 1. However, in other embodiments, any other combustion engine, such as any other suitable gas turbine engine, may be utilized with aspects of the present subject matter.

For instance, the exemplary engine 100 depicted schematically in FIG. 2 generally includes a compressor section having a low pressure compressor 110 and a high pressure compressor 112; a combustion section 114; and a turbine section having a high pressure turbine 116 and a low pressure turbine 118. The exemplary fuel delivery system 200 is in fluid communication with the combustion section 114 for providing fuel to the combustion section 114. The high pressure compressor 112 and high pressure turbine 116 are coupled through a high pressure spool 122, and similarly, the low pressure compressor 110 and low pressure turbine 118 are coupled through a low pressure spool 124. It will be appreciated that, in other embodiments, the exemplary gas turbine engine 100 may have any other suitable number and/or configuration of compressors and turbines. Although not depicted, the exemplary engine 100 may include various engine systems, such as an engine lubrication oil system, etc.

Referring particularly to the fuel oxygen reduction unit 202 of the exemplary fuel delivery system 200, the exemplary fuel oxygen reduction unit 202 of FIG. 2 generally includes a contactor 204 and a fuel gas separator 206. Additionally, the exemplary fuel oxygen reduction unit 202 defines a circulation gas flowpath 208 extending from the fuel gas separator 206 to the contactor 204. In certain exemplary embodiments, the circulation gas flowpath 208 may be formed of any combination of one or more conduits, tubes, pipes, etc., as well as structures of components within the circulation gas flowpath 208.

As will be explained in greater detail below, the fuel oxygen reduction unit 202 generally provides for a flow of stripping gas 210 through the circulation gas flowpath 208 during operation. It will be appreciated that the term "stripping gas" is used herein as a term of convenience to refer to a gas generally capable of performing the functions described herein. The stripping gas 210 flowing through the stripping gas flowpath/circulation gas flowpath 208 may be an actual stripping gas functioning to strip oxygen from the fuel within the contactor 204. Alternatively, the stripping gas 210 flowing through the flowpath 208 may be a sparging gas bubbled through a liquid fuel to reduce an oxygen content of such fuel. For example, as will be discussed in greater detail below, the stripping gas 210 may be an inert gas, such as nitrogen or carbon dioxide ($CO_2$), an inert gas mixture, or some other gas or gas mixture having a relatively low oxygen content.

Moreover, for the exemplary fuel oxygen reduction unit 202 depicted in FIG. 2, the fuel oxygen reduction unit 202 further includes a gas boost pump 212, a gas oxygen reduction unit 214 (which for the embodiment shown is a catalyst 214), and a pre-heater 216. For the embodiment shown, the gas boost pump 212, the catalyst 214, and the pre-heater 216 are each arranged in series flow within the circulation gas flowpath 208. The catalyst 214 is positioned in the circulation gas flowpath 208 for reducing an oxygen content of the flow of stripping gas 210 through the circulation gas flowpath 208. The pre-heater 216 is positioned in thermal communication with the circulation gas flowpath 208 upstream of the catalyst 214. In other embodiments, the pre-heater 216 and the catalyst 214 may be formed as a single unit, such that the unit heats the stripping gas 210 to increase oxygen reduction by the unit. The gas boost pump 212 is positioned in airflow communication with the circulation gas flowpath 208 for increasing a pressure of the flow of stripping gas 210 to the circulation gas flowpath 208. Each of these components will be discussed in greater detail below. Further, it will be appreciated that in other embodiments, the listed components may be provided in any suitable flow order. Moreover, in still other embodiments, the oxygen reduction unit 200 may not define the circulation gas flowpath 208; instead, a stripping gas flow may, e.g., come from an open loop source.

Referring still to the embodiment depicted in FIG. 2, the gas boost pump 212 is configured as a rotary gas pump mechanically coupled to, and driven by, a power source. For the illustrated embodiment, the power source is a first pad 217 of an accessory gearbox (such as accessory gearbox 142 of FIG. 1). Notably, as will be described in greater detail below, the fuel gas separator 206 similarly may be a mechanically-driven fuel gas separator mechanically coupled to, and driven by, a power source. For the embodiment of FIG. 2, the power source driving the fuel gas separator 206 is the same power source driving the gas boost pump 212 (i.e., first pad 217), and more specifically, the gas boost pump 212 and fuel gas separator 206 are mechanically linked through a shaft 220. However, in other embodiments, the gas boost pump 212 and fuel gas separator 206 may be configured in any other suitable manner. For instance, in other embodiments, the gas boost pump 212 may be mechanically separate from the fuel gas separator 206 and driven by an independent power source. Further, in one or more exemplary aspects of the present subject matter, the gas boost pump 212, the fuel gas separator 206, or both may be driven by any other suitable power source, such as an electric machine, a hydraulic or pneumatic motor, etc.

As will be explained in more detail below, for the embodiment of FIG. 2, it will be appreciated that the fuel gas separator 206 generally defines a gas outlet 222, a liquid fuel outlet 224, and an inlet 226. Additionally, the exemplary fuel delivery system 200 generally includes a plurality of fuel lines and, in particular, an inlet fuel line 228 and an outlet fuel line 230. The inlet fuel line 228 is fluidly connected to the contactor 204 for providing a flow of liquid fuel to the contactor 204 (e.g., from a fuel source 235, such as a fuel tank). Additionally, the liquid fuel outlet 224 of the fuel gas separator 206 is fluidly connected to the outlet fuel line 230. In such a manner, the outlet fuel line 230 may receive a deoxygenated flow of liquid fuel 232, as will also be described in greater detail below.

During typical operations, a stripping gas 210 flows from the gas outlet 222 of the fuel gas separator 206, through the circulation gas flowpath 208 in a direction from the fuel gas separator 206 to the contactor 204. More specifically, during typical operations for the depicted embodiment, stripping gas 210 flows from the gas outlet 222 of the fuel gas separator 206 through a pre-heater 216 configured to add heat energy to the gas flowing therethrough (as is explained in more detail below) and to/through the catalyst 214. The stripping gas 210 then flows through the gas boost pump 212, wherein a pressure of the stripping gas 210 is increased to provide for the flow of the stripping gas 210 through the circulation gas flowpath 208. The relatively high pressure stripping gas 210 (i.e., relative to a pressure upstream of the boost pump 212 and the fuel entering the contactor 204) is then provided to the contactor 204, wherein the stripping gas 210 is mixed with a flow of liquid fuel 232 from the inlet fluid line 228 to generate a fuel gas mixture 218. The fuel gas mixture 218 generated within the contactor 204 is provided to the inlet 226 of the fuel gas separator 206.

Generally, it will be appreciated that during operation of the fuel oxygen reduction unit 202, the liquid fuel 232 provided through the inlet fuel line 228 to the contactor 204 may have a relatively high oxygen content. The stripping gas 210 provided to the contactor 204 may have a relatively low oxygen content or other specific chemical structure. Within the contactor 204, the liquid fuel 232 is mixed with the stripping gas 210, resulting in the fuel gas mixture 218. As a result of such mixing, a physical exchange may occur whereby at least a portion of the oxygen within the fuel 232 is transferred to the stripping gas 210, such that the fuel 232 component of the mixture 218 has a relatively low oxygen content (as compared to the fuel 232 provided through inlet fuel line 228) and the stripping gas 210 component of the mixture 218 has a relatively high oxygen content (as compared to the stripping gas 210 provided through the circulation gas flowpath 208 to the contactor 204).

Within the fuel gas separator 206, the relatively high oxygen content stripping gas 210 is generally separated from the relatively low oxygen content fuel 232. As noted above, the exemplary fuel gas separator 206 of FIG. 2 generally is configured as a mechanical fuel gas separator. Accordingly, the fuel gas separator 206 may include one or more paddles or other structures configured to rotate to centrifuge and separate the relatively heavy liquid fuel 232 from the relatively light stripping gas 210, resulting in separate streams of liquid fuel 232 provided through the liquid fuel outlet 224 and stripping gas 210 provided through the gas outlet 222. Notably, however, in other embodiments, any other suitable structure or configuration may be provided for the fuel gas separator 206 capable of separating the fuel gas mixture 218 received through the fuel gas mixture inlet 226 from the contactor 204 into separate streams of liquid fuel 232 and stripping gas 210.

Accordingly, it will be appreciated that the liquid fuel 232 provided to the liquid fuel outlet 224, having interacted with the stripping gas 210, may have a relatively low oxygen content, such that a relatively high amount of heat may be added thereto with a reduced risk of the fuel coking (i.e., chemically reacting to form solid particles that may clog up or otherwise damage components within the fuel flow path). For example, in at least certain exemplary aspects, the fuel 232 provided to the liquid fuel outlet 224 may an oxygen content of less than about five (5) parts per million ("ppm"), such as less than about three (3) ppm, such as less than about two (2) ppm, such as less than about one (1) ppm, such as less than about 0.5 ppm.

Referring still to the schematic view of the fuel oxygen reduction unit 202 in FIG. 2, it will further be appreciated that the exemplary fuel oxygen reduction unit 202 recirculates and reuses the stripping gas 210 (i.e., the stripping gas 210 operates in a substantially closed loop). However, the stripping gas 210 exiting the fuel gas separator 206, having interacted with the liquid fuel 232, may have a relatively high oxygen content. Accordingly, to reuse the stripping gas 210, an oxygen content of the stripping gas 210 from the gas outlet 222 of the fuel gas separator 206 needs to be reduced. For the embodiment depicted, as noted above, the stripping gas 210 flows through the pre-heater 216 to the catalyst 214, where the oxygen content of the stripping gas 210 is reduced. More specifically, within the catalyst 214, the relatively oxygen-rich stripping gas 210 is reacted to reduce the oxygen content thereof. It will be appreciated that catalyst 214 may be configured in any suitable manner to perform such functions. For instance, in certain embodiments, the catalyst 214 may be configured to react the fuel-vapor rich stripping gas 210 with elements inside the catalyst 214 to provide a relatively oxygen-free stripping gas 210 upon exit. As an example, the catalyst 214 may include geometries of catalytic components through which the relatively oxygen-rich stripping gas 210 flows to reduce the oxygen content thereof. Further, in other embodiments any other suitable gas oxygen reduction unit or catalyst 214 may be provided for reducing an oxygen content of the stripping gas 210. For example, in addition to, or in the alternative, the gas oxygen reduction unit or catalyst 214 may utilize a membrane oxygen reduction system, a combustion reduction system, a plasma reduction system, etc.

In one or more of these embodiments, the gas oxygen reduction unit/catalyst 214 may be configured to reduce an oxygen content of the stripping gas 210 by between about twenty-five percent (25%) by mass and about ninety-nine percent (99%) by mass, such as to less than about three percent (3%) oxygen (O2) by mass, such as to less than about one percent (1%) oxygen (O2) by mass.

The resulting relatively low oxygen content gas is then provided through the remainder of the circulation gas flowpath 208 and back to the contactor 204, such that the cycle may be repeated. In such a manner, it will be appreciated that the stripping gas 210 may be any suitable gas capable of undergoing the transitions described above. For example, the stripping gas 210 may be air from, e.g., a core air flowpath of a gas turbine engine including the fuel oxygen reduction unit 202 (e.g., compressed air bled from an HP compressor 112; see FIG. 1). However, in other embodiments, the stripping gas 210 may additionally, or alternatively, be any other suitable gas, such as an inert gas, e.g., nitrogen or carbon dioxide (CO2); an inert gas mixture; or some other gas or gas mixture having a relatively low oxygen content.

Briefly, referring back to the pre-heater 216, it will be appreciated that the catalyst 214 may define a minimum light off temperature (also referred to as an activation temperature) for the stripping gas 210, such that when the stripping gas 210 is below this temperature, the catalyst 214 may not operate as desired. In at least certain exemplary embodiments, the minimum light off temperature may be between about 350 degrees Fahrenheit (350° F.) and about 750 degrees Fahrenheit (750° F.), such as between about 500 degrees Fahrenheit (500° F.) and about 700 degrees Fahrenheit (700° F.). Accordingly, the pre-heater 216 may be configured to heat the stripping gas 210 within the circulation gas flowpath 208 to the minimum light off temperature, or to a temperature above the minimum light off temperature. In at least certain exemplary embodiments, the pre-heater 216 may be an electric heater or a heat exchanger. Specifically, for the embodiment shown, the pre-heater 216 is configured as an electric heater electrically coupled to an electric power source 236. For example, the electric heater may be an electric resistance heater positioned in the circulation gas flowpath 208 to add heat to the flow of stripping gas 210 through the circulation gas flowpath 208. Further, as will be appreciated from the discussion below relating to the control system 254, in certain embodiments, the pre-heater 216 may be configured to provide a varying amount of heat to the flow of stripping gas 210 through the circulation gas flowpath 208 based on, e.g., a temperature of the flow of stripping gas 210 immediately upstream of the pre-heater 216, a temperature of the flow of stripping gas 210 immediately downstream of the pre-heater 216, or other suitable operating parameters.

By way of example, in one or more exemplary embodiments, the pre-heater 216 may be configured to increase a temperature of the stripping gas 210 by at least about fifty degrees Fahrenheit (50° F.), such as by at least about seventy-five degrees Fahrenheit (75° F.), such as up to about seven hundred degrees Fahrenheit (700° F.).

It will be appreciated, however, that in other exemplary embodiments, any other suitable type or configuration of pre-heater 216 may be provided. For instance, referring now briefly to FIG. 3, a schematic view of a fuel delivery system 200 and engine 100 in accordance with another exemplary embodiment is provided. The exemplary fuel delivery system 200 and engine 100 of FIG. 3 may be configured in substantially the same manner as exemplary system 200 and engine 100 described above with reference FIG. 2. For example, the exemplary system 200 of FIG. 3 includes a fuel oxygen reduction unit 202, with the fuel oxygen reduction unit 202 defining a circulation gas flowpath 208 and including a catalyst 214 and a pre-heater 216.

As with the embodiment of FIG. 2, the pre-heater 216 is positioned in thermal communication with the circulation gas flowpath 208 upstream of the catalyst 214 (and downstream of a fuel gas separator 206). However, for the embodiment of FIG. 3, the pre-heater 216 is instead configured as a heat exchanger. The exemplary heat exchanger of FIG. 3 may be in thermal communication with any suitable heat source, such as any suitable engine and/or aircraft heat source. Specifically, for the embodiment shown, the heat exchanger is in thermal communication with at least one of an engine system or an engine flowpath, such as a core air flowpath of the engine 100 (see, e.g., core air flowpath 121 of FIG. 1). More specifically, for the embodiment shown, the heat exchanger/pre-heater 216 is fluidly connected to both a first flowpath 238 configured to provide a flow of thermal fluid from a flowpath heat exchanger 239 (the flowpath heat exchanger 239 being thermally coupled to the flowpath of the engine 100) to the heat exchanger/pre-heater 216 and a second flowpath 240 configured to return the flow of thermal fluid from the heat exchanger/pre-heater 216 to the flowpath of the engine 100. The flowpath heat exchanger 239 may be configured to extract heat from the engine flow path. Notably, however, in other embodiments, the first and second flowpaths 238, 240 may instead be configured to provide and return a flow of lubrication oil to and from, e.g., a lubrication oil system of the engine 100. Additionally or alternatively, in other embodiments, the heat exchanger/pre-heater 216 may be thermally coupled to an intermediate thermal transfer system, which is in turn thermally coupled to one or more systems of the engine 100 or a flowpath of the engine 100.

Additionally, in still other embodiments, the pre-heater 216 may have any other suitable configuration. For example, the pre-heater 216 may be positioned in thermal communication with the circulation gas flowpath 208 of the fuel oxygen reduction unit 202 at a location upstream of the catalyst 214 and may be configured as a recirculating flowpath in airflow communication with circulation gas flowpath 208 downstream of the catalyst 214 and, further, in airflow communication with the circulation gas flowpath 208 upstream of the catalyst 214. The recirculating flowpath may provide at least a portion of the air downstream of the catalyst 214, which may have been combusted or otherwise heated through operation of the catalyst 214, to a location upstream of the catalyst 214 to increase an overall temperature of the flow of stripping gas 210 through the circulation gas flowpath 208 prior such flow stripping gas 210 being provided to the catalyst 214.

Figure 3:
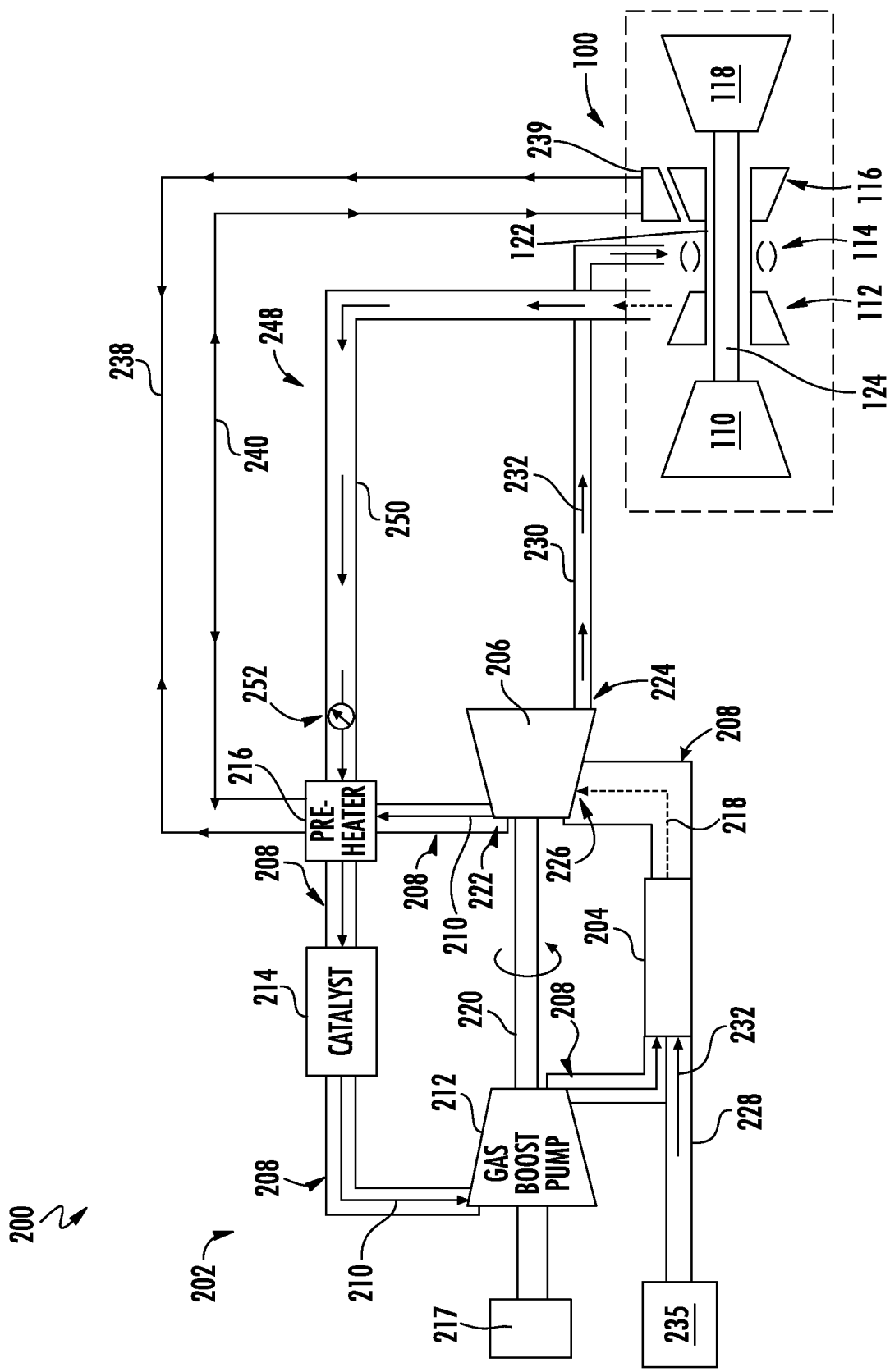
FIG. 3 is a schematic view of a fuel delivery system according to another exemplary embodiment of the present disclosure.

In yet other embodiments, the gas boost pump 212 may be positioned in airflow communication with the circulation gas flowpath 208 upstream of the pre-heater 216 and catalyst 214 (and downstream of a fuel gas separator 206) and also, as will be appreciated, in thermal communication with the circulation gas flowpath 208 upstream of the catalyst 214. In still other embodiments, the pre-heater 216 may be configured as a gas boost pump 212. More specifically, the gas boost pump 212 or the pre-heater 216/gas boost pump 212 may be configured to increase a pressure of the flow of stripping gas 210 through the circulation gas flowpath 208 upstream of the catalyst 214 (and downstream of the fuel gas separator 206). By increasing the pressure of the flow of stripping gas 210, the gas boost pump 212 or pre-heater 216/gas boost pump 212 may further increase a temperature of the flow stripping gas 210 to a temperature above the minimum light off temperature of the catalyst 214. With such an exemplary embodiment, the fuel oxygen reduction unit 202 may not include a separate gas boost pump downstream of the catalyst 214 and upstream of the contactor 204, as illustrated in FIGS. 2 and 3.

Referring back to FIG. 2, it will be appreciated that during operation of the exemplary fuel oxygen reduction unit 202 at least a portion of the stripping gas 210 within the circulation gas flowpath 208 may be lost during, e.g., the separation process. Accordingly, the illustrated exemplary fuel oxygen reduction unit 202 further includes a makeup gas assembly 248 in airflow communication with the circulation gas flowpath 208. More specifically, for the embodiment shown, the makeup gas assembly 248 is in airflow communication with the compressor section of the engine 100 and the circulation gas flowpath 208 upstream of the catalyst 214. For the embodiment depicted, the makeup gas assembly 248 is in airflow communication with the circulation gas flowpath 208 at the pre-heater 216 or upstream of the pre-heater 216 (and downstream of the fuel gas separator 206).

As depicted in FIG. 2, the exemplary makeup gas assembly 248 is in airflow communication with the HP compressor 112 of the compressor section of the engine 100 such that the makeup gas assembly 248 is in airflow communication with the HP compressor 112 for receiving a bleed airflow from the HP compressor 112. For example, in certain embodiments, the makeup gas assembly 248 may be in airflow communication with the HP compressor 112 of the compressor section of the engine 100 at a location where the extracted makeup gas will define a pressure greater than an ambient pressure. Additionally, or alternatively, in certain exemplary aspects of the present subject matter, the HP compressor 112 may include at least four stages of HP compressor rotor blades (see stages 152 of FIG. 1), and the makeup gas assembly 248 may be in airflow communication with the HP compressor 112 at the fourth stage of the HP compressor 112 or downstream of the fourth stage of the HP compressor 112 (e.g., stage 152A of FIG. 1). For example, in certain exemplary aspects, the HP compressor 112 may include at least six stages of HP compressor rotor blades and the makeup gas assembly 248 may be in airflow communication with the HP compressor 112 at the sixth stage of the HP compressor 112 or downstream of the sixth stage of the HP compressor 112 (e.g., stage 152B of FIG. 1).

One benefit of using makeup gas from the above noted locations is the temperature of the makeup gas. However, with other compressors, a desired temperature may be reached at a further upstream position. For example, the HP compressor 112 may define a reference point where the airflow therethrough reaches a reference temperature during a given operating condition (e.g., cruise). With such a configuration, the makeup gas assembly 248 may be in airflow communication with the HP compressor 112 at the reference point or downstream of the reference point. The reference temperature may correspond to the minimum light off temperature for the catalyst 214. As such, the reference temperature may be equal to or greater than about 350 degrees Fahrenheit (350° F.), about 375 degrees Fahrenheit (375° F.), about 400 degrees Fahrenheit (400° F.), or 450 degrees Fahrenheit (450° F.), and up to about 2,000 degrees Fahrenheit (2,000° F.). The reference point may be a particular stage of the HP compressor 112 (or other compressor), such as the fourth stage, or any other suitable stage.

The exemplary makeup gas assembly 248 depicted generally includes makeup gas duct 250 and a makeup gas valve 252. The makeup gas valve 252 may be a pressure differential valve positioned at least partially within the makeup gas duct 250. In such a manner, the pressure differential valve made operate to allow makeup gas through the makeup gas duct to the circulation gas flowpath 208 when a pressure within the circulation gas flowpath 208 falls below a predetermined threshold. For example, in certain embodiments, the pressure differential valve may be a poppet valve.

Briefly, it will be appreciated that although the exemplary makeup gas assembly 248 is depicted being in airflow communication with a location of the compressor section capable of providing the makeup gas flow at a sufficient pressure, in other embodiments, the makeup gas assembly 248 may instead be in airflow communication with the compressor section upstream of the locations depicted and described above (e.g., at an upstream stage of the HP compressor 112, at the LP compressor 110), or elsewhere, and include a separate, dedicated compressor for increasing a pressure of the makeup gas flow to a desired level. For example, the makeup gas assembly 248 may be configured to receive an airflow from a relatively low pressure source (e.g., the LP compressor 110, an ambient location, etc.) and include a dedicated compressor in airflow communication with the duct 250 for increasing a pressure of the makeup gas flow therethrough.

Referring still to the embodiment of FIG. 2, it will be appreciated, however, that by utilizing the makeup gas assembly 248 to provide makeup gas to the circulation gas flowpath 208 from the HP compressor 112 of the compressor section of the engine 100, the makeup gas assembly 248 may further be adding heat to the stripping gas 210 within the circulation gas flowpath 208. Such may further assist with raising a temperature of the flow stripping gas 210 to the circulation gas flowpath 208 upstream of the catalyst 214 to a temperature equal to or above the minimum light off temperature for the catalyst 214. Further, by providing makeup gas to the circulation gas flowpath 208 from the compressor section of the engine 100, the makeup gas assembly 248 may be providing additional oxygen to the flow of stripping gas 210 through the circulation gas flowpath 208 upstream of the catalyst 214, which must additionally be reacted within the catalyst 214.

By way of example only, in certain exemplary embodiments, the fuel oxygen reduction unit 202 may lose between about 0.25 percent (0.25%) and about two (2) percent (2%) of the stripping gas 210 through the separation process. With such a configuration, the makeup gas assembly 248 may be configured to provide a makeup gas to the circulation gas flowpath 208 at a flow rate equal to between about 0.05 percent (0.05%) and about five (5) percent (5%), such as between about 0.25 percent (0.25%) and about three (3) percent (3%), of a maximum rated circulation gas flowpath flow rate. The "maximum rated circulation gas flowpath flow rate" refers to a flowrate of stripping gas 210 through the circulation gas flowpath 208 when the fuel oxygen reduction unit 202 is operating at a maximum rated speed and a designed amount of stripping gas 210 is present in the flowpath 208. Accordingly, in certain exemplary aspects, depending on, e.g., a size of the fuel oxygen reduction unit 202, the makeup gas assembly 248 may be configured to provide makeup gas to the circulation gas flowpath 208 at a flow rate of between about 0.0001 pounds per second and about 0.0025 pounds per second.

Keeping with FIG. 2, it will be appreciated that the exemplary fuel delivery system 200 and fuel oxygen reduction unit 202 further includes a control system 254. More specifically, the exemplary fuel delivery system 200 and fuel oxygen reduction unit 202 includes a plurality of sensors 256, such as a circulation gas flowpath flow sensor 256A positioned downstream of the fuel gas separator 206 and upstream of where the makeup gas assembly 248 meets the circulation gas flowpath 208; a first temperature sensor 256B configured to sense data indicative of a temperature of the flow of stripping gas 210 through the circulation gas flowpath 208 at a location upstream of the pre-heater 216, e.g., at an inlet to the pre-heater 216; a second temperature sensor 256B configured to sense data indicative of a temperature of the flow stripping gas 210 through the circulation gas flowpath 208 at a location downstream of the pre-heater 216 and upstream of the catalyst 214, e.g., at an outlet of the pre-heater 216; and a plurality of third temperature sensors 256B configured to sense data indicative of a temperature of the flow stripping gas 210 through the circulation gas flowpath 208 passing through the catalyst 214. The temperature sensors 256B are described in greater detail below.

Further, the exemplary control system 254 includes a controller 258, with the controller 258 being operably connected to each of the one or more sensors 256, as well as the makeup gas valve 252 of the makeup gas assembly 248 and the pre-heater 216 (or, rather, the power source 236 of the pre-heater 216). Specifically, the controller 258 generally includes a network interface 260. The network interface 260 may be operable with any suitable wired or wireless communications network for communicating data with other components of, e.g., the fuel delivery system 200/fuel oxygen reduction unit 202, the engine 100, and/or other components or systems not depicted. As is illustrated using phantom lines, for the exemplary embodiment of FIG. 2, the network interface 260 utilizes a wireless communication network 262 to communicate data with other components. More particularly, through the network interface 260 of the controller 258 and the wireless communication network 262, the controller 258 is operably coupled to each of the one or more sensors 256, the variable throughput gas valve 252, and the pre-heater 216 (or, rather, the power source 236). It will be appreciated, of course, that although the network interface 260 utilizes the wireless communication network 262 for the exemplary embodiment of FIG. 2, in other embodiments, the network interface 260 may instead utilize a wired communication network or a combination of wired and wireless communication networks.

Referring still to FIG. 2, the controller 258 further includes one or more processors 264 and memory 266. The memory 266 stores data 268 and instructions 270 accessible by the one or more processors 264. The one or more processor(s) 264 can include any suitable processing device, such as a microprocessor, microcontroller, integrated circuit, logic device, and/or other suitable processing device. The one or more memory device(s) 266 can include one or more computer-readable media, including, but not limited to, non-transitory computer-readable media, RAM, ROM, hard drives, flash drives, and/or other memory devices. The instructions 270, when executed by the one or more processors 264, cause the system 254 to perform functions. The instructions 270 within the memory 266 can be any set of instructions that, when executed by the one or more processor(s) 264, cause the one or more processor(s) 264 to perform operations, such as one or more of the operations described herein. In certain exemplary embodiments, the instructions 270 within the memory 266 can be software written in any suitable programming language or can be implemented in hardware. Additionally and/or alternatively, the instructions can be executed in logically and/or virtually separate threads on processor(s) 264. The memory device(s) 266 can further store other data 270 that can be accessed by the processor(s) 264.

In such a manner, it will be appreciated that in at least certain exemplary embodiments, the controller 258 may be configured to receive data from the one or more sensors 256 and may control operations of the fuel oxygen reduction unit 202 in response to the data received from the one or more sensors 256. For example, the exemplary controller 258 may be configured to operate the makeup gas valve 252 in response to data received from the flow rate sensor 256A (e.g., increase a flow of makeup gas in response to receiving data indicative of a relatively low flow rate of stripping gas 210 through the circulation gas flowpath 208, or decrease a flow of makeup gas based on data indicative of a relatively high flow rate of stripping gas 210 through the circulation gas flowpath 208). Additionally and/or alternatively, the exemplary controller 258 may be configured to operate the pre-heater 216 (and/or the makeup gas assembly 248/gas valve 252) in response to receiving data indicative of a temperature of the flow of stripping gas 210 to the circulation gas flowpath 208 upstream of the pre-heater 216, downstream of the pre-heater 216 and upstream of the catalyst 214, and/or downstream of the catalyst 214.

In some embodiments, the control system 254 and/or the controller 258 may be part of automated digital controls (e.g., a Full Authority Digital Engine Control (FADEC) on an aircraft) that control one or more aspects of an engine, such as engine 100. For example, the controller 258 may be, e.g., an Electronic Engine Controller (EEC) or Electronic Control Unit (ECU) of a FADEC, and in addition to the functions described herein, may control fuel flow, engine geometries, and other parameters to optimize performance of the engine 100 during operation, such as during takeoff, flight, and landing for an aircraft. Various parameters, such as the state of flight, state of aircraft systems, and pilot commands, may be communicated using digital signals from a system, such as an avionics system, to the controller 258. As described herein, the controller 258 may include various components for performing various operations and functions, such as the one or more processor(s) 264 and one or more memory device(s) 266. In other embodiments, the controller 258 may perform the specific functions described herein, and one or more other controllers may control various parameters to optimize performance of the engine 100 other than those specific functions.

Figure 4:
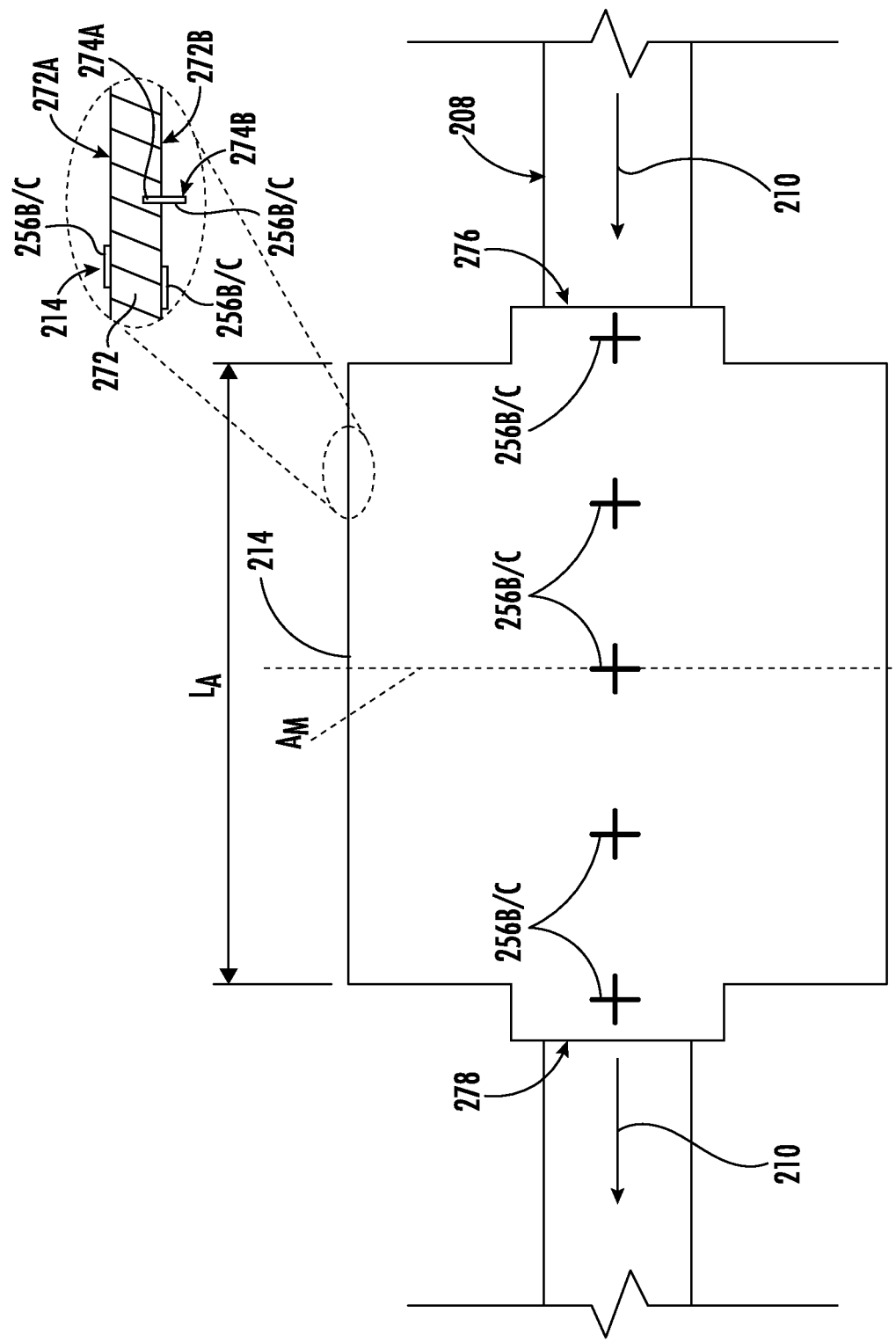
FIG. 4 is a schematic view of a catalyst of a fuel oxygen reduction unit of a fuel delivery system according to an exemplary embodiment of the present subject matter.
Figure 5:
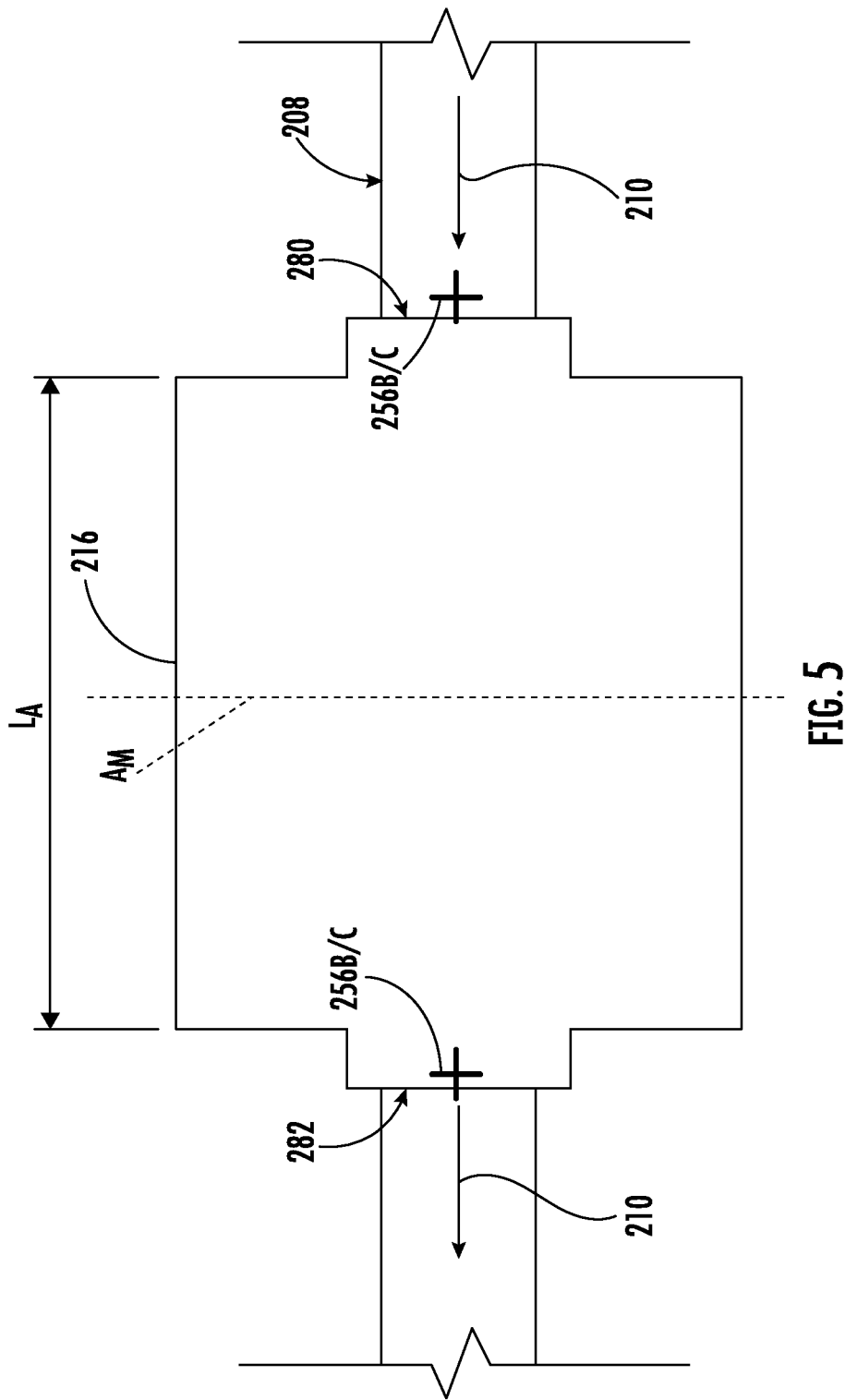
FIG. 5 is a schematic view of a catalyst of a fuel oxygen reduction unit of a fuel delivery system according to another exemplary embodiment of the present subject matter.

Turning now to FIGS. 4 and 5, in exemplary embodiments, the fuel oxygen conversion unit 202 includes features for determining the health of the fuel oxygen conversion unit 202. That is, the fuel oxygen conversion unit 202 includes one or more features for determining whether the unit 202 and/or a component thereof is functioning well enough for fuel oxygen conversion as described herein. For instance, the health of the fuel oxygen conversion unit 202 may depend on whether the gas oxygen reduction unit 214 is adequately reducing an oxygen content of the flow of stripping gas 210 through the circulation gas flowpath 208. More particularly, if the gas oxygen reduction unit 214 (which may be a catalyst 214 as described herein with respect to exemplary embodiments of the fuel oxygen conversion unit 202) becomes fouled, e.g., due to contaminates in the stripping gas 210 and/or residue from fuel vapor in the stripping gas 210, the gas oxygen reduction unit 214 may have a decreased performance, i.e., may have a reduced ability to remove oxygen from the stripping gas 210. While some reduction in performance may be tolerable for the fuel oxygen conversion unit 202 to continue to function within operational limits, if the performance of the gas oxygen reduction unit 214 degrades below a threshold, then the gas oxygen reduction unit 214 may need to be repaired or replaced.

Referring particularly to FIG. 4, a portion of an exemplary fuel oxygen conversion unit 202 of a fuel delivery system 200 as described herein is illustrated. More specifically, FIG. 4 depicts an exemplary gas oxygen reduction unit 214 (which may be a catalyst 214 as described herein) for use in a fuel oxygen conversion unit 202, such as the units 202 illustrated in FIGS. 2 and 3. As shown in FIG. 4, a plurality of sensors 256 are distributed along an axial length $L_A$ of the gas oxygen reduction unit 214. In exemplary embodiments, each sensor 256 may be a temperature sensor 256B such as a thermocouple. In other exemplary embodiments, each sensor 256 may be a pressure sensor 256C. In still other embodiments, the plurality of sensors 256 may comprise both temperature and pressure sensors 256B, 256C. In yet other embodiments, other appropriate sensors 256 for sensing data relative to determining the health of the gas oxygen reduction unit 214, and thereby the fuel oxygen conversion unit 202, may be used in addition to or as an alternative to the temperature sensors 256B and pressure sensors 256C.

The plurality of sensors 256 may be disposed in a variety of locations with respect to the gas oxygen reduction unit 214 along the axial length $L_A$. For example, the plurality of sensors 256 may be disposed in or on a skin 272 of the gas oxygen reduction unit 214. More particularly, the plurality of sensors 256 may be adhered to either an outer surface 272A, an inner surface 272B, or both the outer and inner surfaces 272A, 272B of the gas oxygen reduction unit. For instance, each sensor 256 may be a dielectric sensor that is pasted, taped, or otherwise adhered to the skin 272 of the gas oxygen reduction unit 214. In other embodiments, the plurality of sensors 256 may be embedded in the gas oxygen reduction unit 214 such that at least a portion of each sensor 256 protrudes into the flowpath 208 defined through the gas oxygen reduction unit 214. For example, referring to the cross-section view of the unit 214 provided in FIG. 4, an embedded or immersive sensor 256 may have a first end 274A secured in the gas oxygen reduction unit 214 and an opposite second end 274B may protrude into the flowpath 208 defined through the unit 214. As such, the second end 274B of the sensor 256 may sense, e.g., a bulk flow temperature of the stripping gas 210 flowing through the gas oxygen reduction unit 214.

It will be appreciated that the plurality of sensors 256 may comprise any suitable number of sensors 256. In exemplary embodiments, the plurality of sensors 256 comprises at least three (3) sensors 256 disposed along the axial length $L_A$ of the gas oxygen reduction unit 214, e.g., one sensor 256 at an inlet 276 of the unit 214, one sensor 256 at an outlet 278 of the unit 214, and one sensor 256 disposed between the sensor 256 at the inlet 276 and the sensor 256 at the outlet 278. It will be understood that the inlet 276 of the gas oxygen reduction unit 214 permits an ingress of the stripping gas 210 into the unit 214, and the outlet 278 of the unit 214 permits an egress of the stripping gas 210 from the unit 214. Further, in other exemplary embodiments, the plurality of sensors 256 may comprise five (5) sensors 256, ten (10) sensors 256, between three (3) and ten (10) sensors 256, or more than ten (10) sensors 256. In still other embodiments, the plurality of sensors 256 disposed along the axial length $L_A$ may comprise one sensor 256 per inch (1/in.) of axial length $L_A$, such that each sensor 256 is separated from another sensor 256 by approximately an inch.

As previously described, each sensor 256 of the plurality of sensors 256 may be a temperature sensor 256B or a pressure sensor 256C, or the plurality of sensors 256 may comprise both temperature and pressure sensors 256B, 256C or any other suitable sensor, e.g., for monitoring the health of the fuel oxygen conversion unit 202 as described herein. The sensors 256 may allow, e.g., the controller 258 or FADEC to determine a change in condition (e.g., a change in temperature ($\Delta T$) or a change in pressure ($\Delta P$)) of the stripping gas 210 along the axial length $L_A$ of the gas oxygen reduction unit 214, which may indicate whether the gas oxygen reduction unit 214 is functioning at a performance level to adequately reduce the oxygen content of the stripping gas 210 flowing through the unit 214. Thus, as described in greater detail below, the change in condition of the stripping gas 210 provided by data from the sensors 256 may be indicative of the health of the gas oxygen reduction unit 214 and, therefore, the fuel oxygen conversion unit 202.

Turning now to FIG. 5, a plurality of sensors 256 may be distributed along the pre-heater 216 as an alternative to or in addition to distributing the sensors 256 along the gas oxygen reduction unit 214. FIG. 5 illustrates a portion of an exemplary fuel oxygen conversion unit 202 of a fuel delivery system 200 as described herein. More particularly, FIG. 5 depicts an exemplary pre-heater 216 for use in a fuel oxygen conversion unit 202, such as the units 202 illustrated in FIGS. 2 and 3. As shown in FIG. 5, a plurality of sensors 256 are distributed along an axial length $L_A$ of the pre-heater 216. As described with respect to FIG. 4, the sensors 256 may be temperature sensors 256B, pressure sensors 256C, a combination of temperature and pressure sensors 256B, 256C, or any other suitable sensor, e.g., for monitoring the health of the fuel oxygen conversion unit 202.

In the exemplary embodiment of FIG. 5, one temperature sensor 256B is disposed at an inlet 280 of the pre-heater 216 and another temperature sensor 256B is disposed at an outlet 282 of the pre-heater 216. It will be appreciated that the pre-heater inlet 280 permits an ingress of the stripping gas 210 into the pre-heater 216, and the pre-heater outlet 282 permits an egress of the stripping gas 210 from the pre-heater 216. Thus, the temperature sensors 256B shown in FIG. 5 may allow, e.g., the controller 258 or FADEC to determine a change in temperature ($\Delta T$) of the stripping gas 210 from the pre-heater inlet 280 to the pre-heater outlet 282. The change in temperature ($\Delta T$) of the stripping gas 210 may indicate whether the pre-heater 216 is adequately heating the stripping gas 210 in preparation for reducing the oxygen content of the gas 210 as it passes through the gas oxygen reduction unit 214 downstream of the pre-heater 216. Thus, as described in greater detail below, the change in temperature ($\Delta T$) provided by data from the temperature sensors 256B may be indicative of the health of the pre-heater 216 and, therefore, the fuel oxygen conversion unit 202.

It will be understood that, in other embodiments, the plurality of sensors 256 distributed along the pre-heater 216 may be configured as described above with respect to FIG. 4. For instance, the plurality of sensors 256 may be temperature sensors 256B, pressure sensors 256C, or both (or another suitable type of sensor). Further, the plurality of sensors 256 may be secured to the pre-heater 216 as skin and/or embedded sensors. For example, at least one sensor 256 may be disposed along a skin of the pre-heater 216 such that the sensor 256 is adhered to an outer or inner surface of the pre-heater 216, and/or at least one sensor 256 may be embedded in the pre-heater 216 such that at least a portion of the sensor 256 protrudes into the flow of stripping gas 210 through the pre-heater 216. Moreover, the plurality of sensors 256 may comprise two (2) or more sensors 256, such as two (2), three (3), four (4), five (5), or more sensors 256. The plurality of sensors 256 may be distributed axially over the pre-heater 216, e.g., along an axial length $L_A$ of the pre-heater 216, as shown in FIGS. 4 and 5. In some embodiments, the sensors 256 may be distributed over the pre-heater 256 such that there is one sensor 256 approximately every inch of the axial length $L_A$ of the pre-heater 216.

It will be appreciated, however, that the exemplary fuel oxygen reduction unit 202 described above is provided by way of example only. In other embodiments, the fuel oxygen reduction unit 202 may be configured in any other suitable manner.

Figure 6:
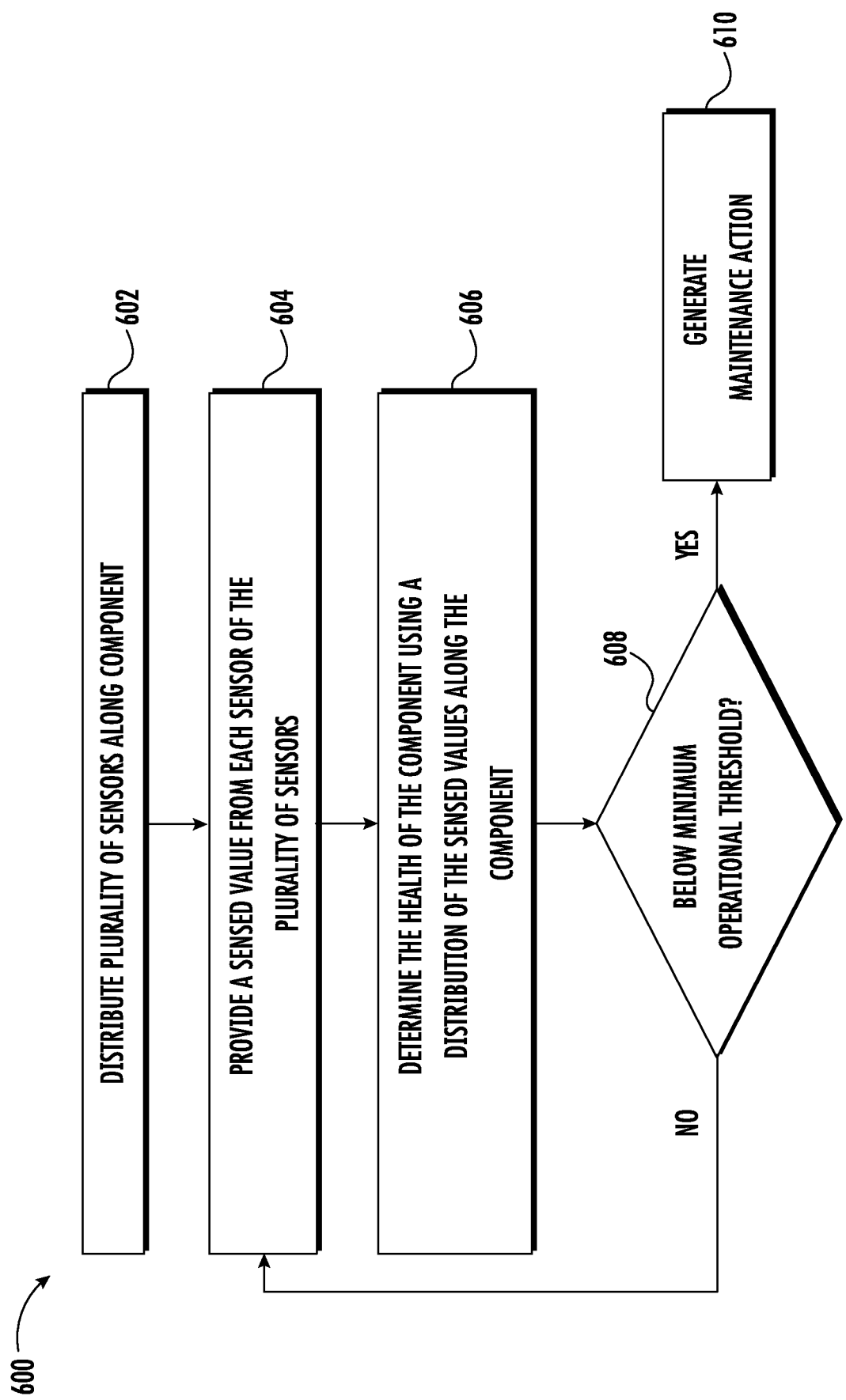
FIG. 6 is a flow diagram of a method for monitoring the health of a fuel oxygen reduction unit according to an exemplary embodiment of the present subject matter.

Referring now to FIG. 6, a flow diagram is provided of a method 600 of monitoring the health of a fuel oxygen conversion unit for a vehicle or an engine of the vehicle, such as a gas turbine engine of an aircraft, in accordance with an exemplary aspect of the present subject matter. In at least certain exemplary aspects, the method 600 may be utilized to operate one or more of the exemplary fuel delivery systems 200 and fuel oxygen reduction units 202 described above with reference to FIGS. 1 through 5.

For the exemplary aspect depicted in FIG. 6, the method 600 generally includes at (602) distributing a plurality of sensors along a component. For example, as described above with respect to FIG. 4, distributing a plurality of sensors along a component may comprise distributing a plurality of temperature sensors 256B, pressure sensors 256C, and/or both temperature and pressure sensors 256B, 256C along an axial length $L_A$ of a gas oxygen reduction unit 214 (such as a catalyst 214) of a fuel oxygen conversion unit 202. As another example, as described with respect to FIG. 5, distributing a plurality of sensors along a component may comprise distributing a plurality of temperature sensors 256B, pressure sensors 256C, and/or both temperature and pressure sensors 256B, 256C along an axial length $L_A$ of a pre-heater 216 of a fuel oxygen conversion unit 202. In some embodiments, a plurality of sensors 256 may be distributed along both of the gas oxygen reduction unit 214 and the pre-heater 216.

Further, as described with respect to FIGS. 4 and 5, distributing the plurality of sensors 256 may comprise disposing each sensor 256 of the plurality of sensors 256 along a skin of the component such that each sensor 256 of the plurality of sensors 256 is disposed along an inner surface or an outer surface of the component. For instance, where the component is a gas oxygen reduction unit 214, each sensor 256 may be disposed along the skin 272 of the unit 214 such that the sensors 256 are disposed along an outer surface 272A or an inner surface 272B of the unit 214. In other embodiments, the sensors 256 may be disposed along both the outer and inner surfaces 272A, 272B of the gas oxygen reduction unit 214. The plurality of sensors 256 may be disposed along the skin 272, e.g., by adhering the sensors 256 using a paste, tape, or other means for adhering the sensors 256, which may be dielectric sensors as described above.

In other embodiments, distributing the plurality of sensors 256 may comprise embedding each sensor 256 of the plurality of sensors 256 in the component such that at least a portion of each sensor 256 protrudes into a stripping gas 210 flowpath defined through the component. As an example, where the component is a pre-heater 216, each sensor 256 may be embedded in the pre-heater 216 such that an end 274B of the sensor 256 protrudes into the flow of stripping gas 210 through the pre-heater 216. It will be appreciated that, as described with respect to FIGS. 4 and 5, the plurality of sensors 256 may be both skin and embedded sensors, i.e., both disposed along the skin of the gas oxygen reduction unit 214 and/or pre-heater 216 and embedded in the gas oxygen reduction unit 214 and/or pre-heater 216.

As further illustrated in FIG. 6, the method 600 also may include at (604) providing a sensed value from each sensor 256 of the plurality of sensors 256 distributed along the component. For example, in some embodiments, each sensor 256 of the plurality of sensors 256 is a temperature sensor 256B, and the sensed value provided from each temperature sensor 256B is a temperature. In other embodiments, each sensor 256 of the plurality of sensors 256 is a pressure sensor 256C, and the sensed value provided from each pressure sensor 256C is a pressure. In yet other embodiments, the plurality of sensors 256 comprises temperature sensors 256B and pressure sensors 256C, and the sensed value provided from each sensor 256 of the plurality of sensors 256 is either a temperature or a pressure.

As previously described, the sensors 256 may be distributed such that the sensed value is provided from a variety of locations spaced axially along the component, e.g., the gas oxygen reduction unit 214 or the pre-heater 216. For instance, one sensor 256 may be disposed at the inlet 280 of the pre-heater 216 and another sensor 256 may be disposed at the outlet 282 of the pre-heater 216 such that the sensed values are provided from the inlet 280 and outlet 282 of the pre-heater 216. As another example, three or more sensors 256 may be axially distributed along the gas oxygen reduction unit 214, such that the sensed values are provided from multiple axial locations of the gas oxygen reduction unit 214.

Keeping with FIG. 6, the method 600 generally includes at (606) determining the health of the component using a distribution of the sensed values along the component. For example, determining the health of the gas oxygen reduction unit 214 and/or the pre-heater 216 (and, thereby, the fuel oxygen conversion unit 202) may comprise analyzing the distribution of the sensed values along the axial length $L_A$ of the gas oxygen reduction unit 214 and/or the pre-heater 216. In some embodiments, determining the health of the fuel oxygen conversion unit 202 comprises comparing the distribution of the sensed values to a known distribution of the sensed values. More particularly, a baseline distribution of temperatures and/or pressures may be established, e.g., for a gas oxygen reduction unit 214 and pre-heater 216 known to be substantially free from fouling or contamination, such as a new or recently serviced gas oxygen reduction unit 214 and pre-heater 216. The baseline distribution thereby serves as the known distribution, i.e., how the temperature and/or pressure values are expected to be axially distributed along the gas oxygen reduction unit 214 and/or pre-heater 216 when the component (unit 214 and/or pre-heater 216) is functioning or preforming at a high or optimal level.

In exemplary embodiments, a known or baseline temperature distribution for the gas oxygen reduction unit 214 may comprise a distribution that decreases from the sensor 256 nearest the inlet 276 to the sensor 256 nearest the outlet 278, i.e., the temperature decreases as the flow of stripping gas 210 moves downstream through the unit 214. Stated differently, a known or baseline temperature distribution may comprise a highest or hottest temperature measured at the first temperature sensor 256B encountered by the stripping gas 210 and the lowest or coldest temperature measured at the last temperature sensor 256B encountered by the stripping gas 210, with the temperatures decreasing at each successive temperature sensor 256B from the first to the last. That is, the reaction that occurs within the gas oxygen reduction unit 214 to remove oxygen from the stripping gas 210, which is generally an exothermic reaction, may be concentrated at an upstream portion of the unit 214 such that the temperature decreases over an axial distribution from the inlet 276 to the outlet 278. Thus, in exemplary embodiments, if the actual or measured axial temperature distribution does not decrease from the sensor 256B nearest the inlet 276 to the sensor 256B nearest the outlet 278, it may be inferred that the gas oxygen reduction unit 214 is at least functioning at reduced performance.

As one example, illustrated in FIG. 4, a gas oxygen reduction unit 214 may include five (5) temperature sensors 256B distributed along the axial length $L_A$ of the unit 214 from the inlet 276 to the outlet 278. That is, in an exemplary embodiment, one temperature sensor 256B may be disposed at or near the inlet 276, one temperature sensor 256B may be disposed at or near the outlet 278, and the remaining three temperature sensors 256B may be dispersed between the inlet sensor 256B and the outlet sensor 256B. In some embodiments, the five (5) temperature sensors 256B may be substantially equidistant from one another, but the sensors 256B need not be equally spaced apart. During operation of the fuel system 200, the temperature sensed by each of the five (5) temperature sensors 256B may be collected by, e.g., the controller 258 or FADEC (or a component thereof) and compared to a known or baseline temperature distribution in which the temperature decreases from the inlet sensor to the outlet sensor. In an exemplary embodiment, a first comparison may show that the actual or measured temperatures follow this distribution, but a second comparison, using temperature data from a later time, may show that the actual or measured temperatures decrease from the next temperature sensor 256B downstream from the inlet temperature sensor 256B to the outlet temperature sensor 256B. A third comparison, using temperature data from yet a later time, may show that the actual or measured temperatures decrease from the third temperature sensor 256B downstream from the inlet temperature sensor 256B to the outlet temperature sensor 256B. That is, the gas oxygen reduction unit 214 may become fouled in its hottest region first, such that the reaction taking place within the unit 214 moves farther downstream from the inlet 278 as the unit 214 becomes fouled (e.g., from metals or the like within the fuel). As such, less reacting may be occurring within the gas oxygen reduction unit 214 and the unit 214 may have a reduced performance. A comparison between the actual or measured axial temperature distribution and the known or baseline axial temperature distribution that shows the hottest area within the gas oxygen reduction unit 214 has moved downstream from the inlet 276 may trigger a maintenance action, such as repair or replacement of the unit 214. In some embodiments, the maintenance action may not be triggered until the measured axial temperature distribution reveals the hottest area within the gas oxygen reduction unit 214 is past an axial midpoint $A_M$ between the inlet 276 and the outlet 278, i.e., that the hottest area is axially closer to the outlet 278 than the inlet 276. In other embodiments, the maintenance action may not be triggered until there are a lack of temperature spikes or hot zones in the measured axial temperature distribution, i.e., the temperature measurements from the temperature sensors 256B show that no one area of the gas oxygen reduction unit 214 is hotter than another area, which may indicate that all unfouled reaction zones or areas within the unit 214 have been exhausted.

By comparing the current distribution of the sensed values to the baseline or known distribution, the health of the gas oxygen reduction unit 214 and/or the pre-heater 216 (and, thereby, the fuel oxygen conversion unit 202) can be determined. More specifically, a minimum operational threshold may be established, e.g., using the baseline or known distribution of the sensed values. The minimum operational threshold may be a set of sensed values below which the component, e.g., the gas oxygen reduction unit 214 or pre-heater 216, is not operating at a level to adequately perform its function in the fuel oxygen conversion unit. For instance, below the minimum operational threshold for the gas oxygen reduction unit 214, the gas oxygen reduction unit 214 is not removing sufficient oxygen from the stripping gas 210 to enable the stripping gas 210 to absorb oxygen from the liquid fuel 232 at a location downstream of the gas oxygen reduction unit 214 as described above. As another example, below the minimum operational threshold for the pre-heater 216, the pre-heater 216 is not heating the stripping gas 210 to a sufficient temperature for removal of oxygen from the stripping gas 210 at a location downstream of the pre-heater 216 as described herein.

It will be appreciated that, for the pre-heater 216, the sensed values provided by the plurality of sensors 256 may be a direct indication of the minimum operational threshold. For example, whether the pre-heater 216 is heating the stripping gas 210 to a minimum operational temperature threshold may be directly determined from the temperature measurements provided by a plurality of temperature sensors 256B distributed along the pre-heater 216. In other embodiments, for example where the pre-heater 216 is powered by an electrical power input, the change in temperature ($\Delta T$) between the pre-heater inlet 280 and the pre-heater outlet 282 may be compared to a power input to the pre-heater 216 to determine the efficiency of the pre-heater 216. That is, a minimum operational threshold in terms of pre-heater efficiency may be established, such that the health of the pre-heater 216 may be determined by assessing the power input required to achieve the $\Delta T$ calculated from the measured sensed temperature values. For instance, if the calculated $\Delta T$ between the pre-heater inlet 280 and pre-heater outlet 282 is below a minimum $\Delta T$ for the power input required to achieve the calculated $\Delta T$, then the health of the pre-heater 216 may be determined to be below a minimum operational threshold, which may trigger maintenance of the pre-heater 216 as described herein.

For the gas oxygen reduction unit 214, the sensed values provided by the plurality of sensors 256 may allow an inference as to whether the unit 214 is functioning at an adequate level. That is, the minimum operational threshold does not indicate the amount of oxygen (O2) the gas oxygen reduction unit 214 is actually removing from the stripping gas 210. Instead, the temperature or pressure (or other value indicative of the functioning of the unit 214) is an indirect measure of how the gas oxygen reduction unit 214 is functioning. More particularly, the gas oxygen reduction unit 214 generally removes oxygen from the stripping gas 210 in an exothermic reaction. Therefore, the temperature and/or pressure of the stripping gas 210 as it moves through the gas oxygen reduction unit 214 may indicate if the exothermic reaction is proceeding as expected, e.g., whether the temperature and/or pressure at a given time during operation of the unit 214 are comparable to known or baseline temperature and/or pressure values or a distribution of such temperature and/or pressure values as described above.

However, in some embodiments, the temperature and/or pressure values sensed or measured by the sensors 256 may be used to determine the amount of oxygen the gas oxygen reduction unit 214 is extracting from the stripping gas 210 passing therethrough. For instance, knowing the flowrate of the stripping gas 210 through the gas oxygen reduction unit 214 and the temperature and/or pressure distribution over the gas oxygen reduction unit 214, the quantity of oxygen extracted from the stripping gas 210 may be determined, e.g., by the controller 258, FADEC, or a component thereof. Accordingly, the determined or calculated quantity of extracted oxygen may be compared to a known or expected quantity of extracted oxygen to determine the health of the gas oxygen reduction unit 214. More particularly, in addition to or as an alternative to comparing the temperature or pressure distribution to a known distribution to determine the health of the gas oxygen reduction unit 214, the amount of oxygen determined or calculated to have been extracted from the stripping gas 210 at a given time may be compared to an amount of oxygen expected to be extracted by the gas oxygen reduction unit 214 at the same stripping gas flowrate. Thus, the temperatures and/or pressures (or other suitable values as described herein) sensed by the sensors 256 along the gas oxygen reduction unit 214 may allow an inference as to whether sufficient oxygen is being extracted from the stripping gas 210 for adequate operation of the fuel oxygen conversion unit 202. Additionally or alternatively, the temperatures and/or pressures (or other suitable values) may be used to determine the amount of extracted oxygen, which in turn may be compared to a known or baseline value of extracted oxygen to determine whether sufficient oxygen is being extracted from the stripping gas 210 for adequate operation of the fuel oxygen conversion unit 202. Therefore, in exemplary embodiments, the minimum operational threshold may be a distribution of temperature and/or pressure values (or other suitable values) or may be an amount of oxygen.

As further illustrated in FIG. 6, the method 600 may include at (608) determining whether the health of the component, e.g., the gas oxygen reduction unit 214 and/or the pre-heater 216 (which indicate the health of the fuel oxygen conversion unit 202), is below a minimum operational threshold. For instance, if the health of the gas oxygen reduction unit 214 is below a minimum operational threshold, the distribution of temperatures and/or pressures sensed by temperature sensors 256B and/or 256C distributed along the unit 214 is below a threshold distribution of temperatures and/or pressures, or the calculated amount of oxygen being extracted by the unit 214 is below a threshold amount of oxygen. As another example, if the health of the pre-heater 216 is below a minimum operational threshold, the distribution of temperatures and/or pressures sensed by temperature sensors 256B and/or 256C distributed along the pre-heater 216 is below a threshold distribution of temperatures and/or pressures.

As shown at (610) in FIG. 6, if the health of the component is below the minimum operational threshold, the method 600 may include generating a maintenance action for maintenance of the fuel oxygen conversion unit 202. In some embodiments, the maintenance action may be replacement or repair of the gas oxygen reduction unit 214. In other embodiments, the maintenance action may be replacement or repair of the pre-heater 216. Which component (e.g., the gas oxygen reduction unit 214 and/or the pre-heater 216) is repaired or replaced may be determined by which component has sensors 256 distributed thereon to provide data indicative of the health of the component and, thus, the fuel oxygen conversion unit 202. In yet other embodiments, the maintenance action may be replacement or repair of the entire fuel oxygen conversion unit 202. For example, the fuel oxygen conversion unit 202 may be packaged as a single replaceable unit such that whether the sensors 256 provide data with respect to the gas oxygen reduction unit 214 and/or the pre-heater 216, the entire fuel oxygen conversion unit 202 may be replaced with a new unit 202 in the fuel system 200 when the health of the unit 214 and/or the pre-heater 216 is below the minimum operational threshold.

Referring still to FIG. 6, if the health of the component is above the minimum operational threshold as determined at (610), the method 600 may return to (604) and continue to provide the sensed value from each sensor 256 of the plurality of sensors 256. Accordingly, the method 600 may include repeatedly providing the sensed value from each sensor 256 of the plurality of sensors 256 and determining the health of the fuel oxygen conversion unit 202 (which may correspond to the health of the gas oxygen reduction unit 214 and/or the pre-heater 216) as described above until the health of the fuel oxygen conversion unit 202 is below the minimum operational threshold. That is, the fuel system 200 may continue to operate as described herein and the health of the fuel oxygen conversion unit 202 may be continuously monitored during such operation until the health of the unit 202 is below the minimum operational threshold and the maintenance action is generated.

Accordingly, the present subject matter provides methods and apparatus for monitoring the health of a fuel oxygen conversion unit, which, e.g., may be part of a fuel system for a vehicle or an engine of a vehicle, such as a gas turbine engine of an aircraft. As described herein, measurements (e.g., temperature and/or pressure) can be obtained that may be used to calculate the amount of oxygen reacting in a fuel oxygen conversion system and, therefore, the oxygen being removed from the fuel. The amount of oxygen being removed from the fuel may indicate whether the system, or a particular component within the system, is functioning at an adequate performance level, i.e., whether sufficient oxygen is being removed for continued operation of the system without maintenance. Such measurements also may provide data on an amount and areas of poisoning inside, e.g., a gas oxygen reduction unit or catalyst that will provide details on when/how much maintenance is required. As described herein, in exemplary embodiments, the health of a catalytic process may be determined by measuring the catalyst axial skin temperature distribution and/or by measuring the bulk flow axial temperature distribution within the catalyst. The measured or actual axial temperature distribution may be compared to a known or control axial temperature distribution to assess the health of the catalytic process. Further, a maintenance action may be assigned for the catalyst based on the comparative temperature distribution. In other embodiments, to assess the health of the catalyst or gas oxygen reduction unit (and thereby the fuel oxygen system), the temperature measurements may be used to determine the amount of oxygen being removed from the fuel and/or pressure measurements may be used instead of or in addition to temperature measurements. In still other embodiments, the temperature and/or pressure measurements may be taken with respect to a pre-heater or other component of the fuel oxygen system and the health of the system determined at least in part from those temperature and/or pressure measurements.

Further aspects of the invention are provided by the subject matter of the following clauses:

1. A method of monitoring the health of a fuel oxygen conversion unit for a vehicle or an engine of the vehicle, the method comprising providing a distribution of sensed values obtained from a plurality of sensors distributed along an axial length of a gas oxygen reduction unit of the fuel oxygen conversion unit and determining the health of the fuel oxygen conversion unit from the distribution.

2. The method of any preceding clause, wherein each sensor of the plurality of sensors is a temperature sensor, and wherein the sensed value provided from each temperature sensor is a temperature.

3. The method of any preceding clause, wherein each sensor of the plurality of sensors is a pressure sensor, and wherein the sensed value provided from each pressure sensor is a pressure.

4. The method of any preceding clause, wherein the plurality of sensors comprises temperature sensors and pressure sensors, and wherein the sensed value provided from each sensor of the plurality of sensors is either a temperature or a pressure.

5. The method of any preceding clause, wherein determining the health of the fuel oxygen conversion unit comprises comparing the distribution of the sensed values to a known distribution of the sensed values.

6. The method of any preceding clause, further comprising, if the health of the fuel oxygen conversion unit is below a minimum operational threshold, generating a maintenance action for maintenance of the fuel oxygen conversion unit.

7. The method of any preceding clause, wherein the maintenance action is replacement of the gas oxygen reduction unit.

8. The method of any preceding clause, wherein the maintenance action is repair of the gas oxygen reduction unit.

9. The method of any preceding clause, further comprising, if the health of the fuel oxygen conversion unit is above a minimum operational threshold, returning to providing the sensed value from each sensor of the plurality of sensors.

10. The method of any preceding clause, further comprising repeatedly providing the sensed value from each sensor of the plurality of sensors and determining the health of the fuel oxygen conversion unit using the distribution of the sensed values along the axial length until the health of the fuel oxygen conversion unit is below the minimum operational threshold.

11. The method of any preceding clause, further comprising distributing the plurality of sensors along the axial length of the gas oxygen reduction unit prior to providing the sensed value from each sensor of the plurality of sensors.

12. The method of any preceding clause, wherein distributing the plurality of sensors along the axial length of the gas oxygen reduction unit comprises disposing each sensor of the plurality of sensors on a skin of the gas oxygen reduction unit such that each sensor of the plurality of sensors is disposed along an inner surface or an outer surface of the gas oxygen reduction unit.

13. The method of any preceding clause, wherein distributing the plurality of sensors along the axial length of the gas oxygen reduction unit comprises embedding each sensor of the plurality of sensors in the gas oxygen reduction unit such that at least a portion of each sensor protrudes into a flowpath defined through the gas oxygen reduction unit.

14. The method of any preceding clause, wherein the gas oxygen reduction unit is positioned in a circulation gas flowpath defined from a fuel gas separator to a contactor of the fuel oxygen conversion unit, the gas oxygen reduction unit positioned in the circulation gas flowpath for reducing an oxygen content of a flow of stripping gas through the circulation gas flowpath.

15. The method of any preceding clause, wherein the gas oxygen reduction unit is a catalyst.

16. A fuel oxygen conversion unit for a vehicle or an engine of the vehicle comprising a contactor; a fuel gas separator, the fuel oxygen conversion unit defining a circulation gas flowpath from the fuel gas separator to the contactor; and a gas oxygen reduction unit positioned in the circulation gas flowpath for reducing an oxygen content of a flow of stripping gas through the circulation gas flowpath, wherein a plurality of sensors are distributed along an axial length of the gas oxygen reduction unit.

17. The fuel oxygen conversion unit of any preceding clause, wherein the plurality of sensors are disposed on a skin of the gas oxygen reduction unit.

18. The fuel oxygen conversion unit of any preceding clause, wherein the plurality of sensors are disposed on a skin of the gas oxygen reduction unit such that each sensor of the plurality of sensors is disposed along an inner surface or an outer surface of the gas oxygen reduction unit.

19. The fuel oxygen conversion unit of any preceding clause, wherein the plurality of sensors are embedded in the gas oxygen reduction unit such that at least a portion of each sensor protrudes into a flowpath defined through the gas oxygen reduction unit.

20. The fuel oxygen conversion unit of any preceding clause, wherein the plurality of sensors comprises at least three temperature sensors.

21. The fuel oxygen conversion unit of any preceding clause, wherein the plurality of sensors comprises at least three pressure sensors.

22. The fuel oxygen conversion unit of any preceding clause, further comprising a pre-heater positioned in thermal communication with the circulation gas flowpath upstream of the gas oxygen reduction unit and a gas boost pump downstream of the gas oxygen reduction unit and upstream of the contactor.

23. The fuel oxygen conversion unit of any preceding clause, wherein the gas oxygen reduction unit is a catalyst.

24. A method of monitoring the health of a fuel oxygen conversion unit for a vehicle or an engine of the vehicle, the method comprising providing a temperature from each temperature sensor of a plurality of temperature sensors, the plurality of temperature sensors distributed axially along a pre-heater of the fuel oxygen conversion unit, the pre-heater disposed upstream of a gas oxygen reduction unit of the fuel oxygen conversion unit; and determining the health of the fuel oxygen conversion unit using a change in temperature from an inlet to an outlet of the pre-heater.

25. The method of any preceding clause, wherein determining the health of the fuel oxygen conversion unit comprises comparing the change in temperature to a known change in temperature from the inlet to the outlet of the pre-heater.

26. The method of any preceding clause, further comprising, if the health of the fuel oxygen conversion unit is below a minimum operational threshold, generating a maintenance action for maintenance of the fuel oxygen conversion unit.

27. The method of any preceding clause, wherein the maintenance action is replacement of the pre-heater.

28. The method of any preceding clause, wherein the maintenance action is repair of the pre-heater.

29. The method of any preceding clause, further comprising, if the health of the fuel oxygen conversion unit is above a minimum operational threshold, returning to providing the temperature from each temperature sensor of the plurality of temperature sensors.

30. The method of any preceding clause, further comprising repeatedly providing the temperature from each temperature sensor of the plurality of temperature sensors and determining the health of the fuel oxygen conversion unit using the change in temperature from the inlet to the outlet of the pre-heater until the health of the fuel oxygen conversion unit is below the minimum operational threshold.

31. The method of any preceding clause, further comprising distributing the plurality of temperature sensors axially along the pre-heater prior to providing the temperature from each temperature sensor of the plurality of temperature sensors.

32. The method of any preceding clause, wherein distributing the plurality of temperature sensors axially along the pre-heater comprises disposing each temperature sensor of the plurality of temperature sensors on a skin of the pre-heater such that each temperature sensor of the plurality of temperature sensors is disposed along an inner surface or an outer surface of the pre-heater.

33. The method of any preceding clause, wherein distributing the plurality of temperature sensors axially along the pre-heater comprises embedding each temperature sensor of the plurality of temperature sensors in the pre-heater such that at least a portion of each temperature sensor protrudes into a flowpath defined through the pre-heater.

34. The method of any preceding clause, wherein the pre-heater is positioned in a circulation gas flowpath defined from a fuel gas separator to a contactor of the fuel oxygen conversion unit, the pre-heater positioned in the circulation gas flowpath for increasing a temperature of a flow of stripping gas through the circulation gas flowpath upstream of a gas oxygen reduction unit.

35. A method of monitoring the health of a fuel oxygen conversion unit for a vehicle or an engine of the vehicle, the method comprising providing a sensed value from each sensor of a plurality of sensors distributed along an axial length of a pre-heater of the fuel oxygen conversion unit and determining the health of the fuel oxygen conversion unit using a distribution of the sensed values along the axial length.

36. The method of any preceding clause, wherein each sensor of the plurality of sensors is a temperature sensor, and wherein the sensed value provided from each temperature sensor is a temperature.

37. The method of any preceding clause, wherein each sensor of the plurality of sensors is a pressure sensor, and wherein the sensed value provided from each pressure sensor is a pressure.

38. The method of any preceding clause, wherein the plurality of sensors comprises temperature sensors and pressure sensors, and wherein the sensed value provided from each sensor of the plurality of sensors is either a temperature or a pressure.

39. The method of any preceding clause, wherein determining the health of the fuel oxygen conversion unit comprises comparing the distribution of the sensed values to a known distribution of the sensed values.

40. The method of any preceding clause, further comprising, if the health of the fuel oxygen conversion unit is below a minimum operational threshold, generating a maintenance action for maintenance of the fuel oxygen conversion unit.

41. The method of any preceding clause, wherein the maintenance action is replacement of the pre-heater.

42. The method of any preceding clause, wherein the maintenance action is repair of the pre-heater.

43. The method of any preceding clause, further comprising, if the health of the fuel oxygen conversion unit is above a minimum operational threshold, returning to providing the sensed value from each sensor of the plurality of sensors.

44. The method of any preceding clause, further comprising repeatedly providing the sensed value from each sensor of the plurality of sensors and determining the health of the fuel oxygen conversion unit using the distribution of the sensed values along the axial length until the health of the fuel oxygen conversion unit is below the minimum operational threshold.

45. The method of any preceding clause, further comprising distributing the plurality of sensors along the axial length of the pre-heater prior to providing the sensed value from each sensor of the plurality of sensors.

46. The method of any preceding clause, wherein distributing the plurality of sensors along the axial length of the pre-heater comprises disposing each sensor of the plurality of sensors on a skin of the pre-heater such that each sensor of the plurality of sensors is disposed along an inner surface or an outer surface of the pre-heater.

47. The method of any preceding clause, wherein distributing the plurality of sensors along the axial length of the pre-heater comprises embedding each sensor of the plurality of sensors in the pre-heater such that at least a portion of each sensor protrudes into a flowpath defined through the pre-heater.

48. The method of any preceding clause, wherein the pre-heater is positioned in a circulation gas flowpath defined from a fuel gas separator to a contactor of the fuel oxygen conversion unit, the pre-heater positioned in the circulation gas flowpath for increasing a temperature of a flow of stripping gas through the circulation gas flowpath upstream of a gas oxygen reduction unit.

49. A fuel oxygen conversion unit for a vehicle or an engine of the vehicle comprising a contactor; a fuel gas separator, the fuel oxygen conversion unit defining a circulation gas flowpath from the fuel gas separator to the contactor; and a gas oxygen reduction unit positioned in the circulation gas flowpath for reducing an oxygen content of a flow of stripping gas through the circulation gas flowpath, wherein a plurality of sensors are distributed along an axial length of the gas oxygen reduction unit.

50. The fuel oxygen conversion unit of any preceding clause, wherein the plurality of sensors are disposed on a skin of the gas oxygen reduction unit.

51. The fuel oxygen conversion unit of any preceding clause, wherein the plurality of sensors are disposed on a skin of the gas oxygen reduction unit such that each sensor of the plurality of sensors is disposed along an inner surface or an outer surface of the gas oxygen reduction unit.

52. The fuel oxygen conversion unit of any preceding clause, wherein the plurality of sensors are embedded in the gas oxygen reduction unit such that at least a portion of each sensor protrudes into a flowpath defined through the gas oxygen reduction unit.

53. The fuel oxygen conversion unit of any preceding clause, wherein the plurality of sensors comprises at least three temperature sensors.

54. The fuel oxygen conversion unit of any preceding clause, wherein the plurality of sensors comprises at least three pressure sensors.

55. The fuel oxygen conversion unit of any preceding clause, further comprising a pre-heater positioned in thermal communication with the circulation gas flowpath upstream of the gas oxygen reduction unit and a gas boost pump downstream of the gas oxygen reduction unit and upstream of the contactor.

56. The fuel oxygen conversion unit of any preceding clause, wherein the gas oxygen reduction unit is a catalyst.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A method of monitoring the health of a fuel oxygen conversion unit for a vehicle or an engine of the vehicle, the method comprising:
    (a) receiving a plurality of sensed temperature values obtained from a plurality of temperature sensors distributed along an axial length of a gas oxygen reduction unit of the fuel oxygen conversion unit, wherein the plurality of temperature sensors includes a first temperature sensor disposed upstream from an axial midpoint of the gas oxygen reduction unit, a second temperature sensor disposed downstream from the axial midpoint, and a third temperature sensor disposed axially between the first temperature sensor and the second temperature sensor;
    (b) determining, using the plurality of sensed temperature values, whether a stripping gas passing through the gas oxygen reduction unit has undergone a change in temperature along the axial length of the gas oxygen reduction unit;
    (c) monitoring a change in temperature of the stripping gas in a pre-heater disposed upstream of the gas oxygen reduction unit;
    (d) if the stripping gas has undergone the change in temperature along the axial length of the gas oxygen reduction unit such that the temperature of the stripping gas associated with the gas oxygen reduction unit is below a minimum operational threshold or if the stripping gas has undergone the change in temperature in the pre-heater such that the temperature of the stripping gas associated with the pre-heater is below a minimum operations threshold, instructing a control system to generate a maintenance action for maintenance of the fuel oxygen conversion unit such that the maintenance action mitigates fouling of a combustion system for the vehicle or the engine of the vehicle caused by a fuel having excess oxygen from a faulty fuel oxygen conversion unit; and
    (e) if the stripping gas has undergone the change in temperature along the axial length of the gas oxygen reduction unit such that the temperature of the stripping gas associated with the gas oxygen reduction unit is above a minimum operational threshold or if the stripping gas has undergone the change in temperature in the pre-heater such that the temperature of the stripping gas associated with the pre-heater is above a minimum operations threshold, instructing a control system to repeat steps (a) through (d) to actively monitor and mitigate fouling of a combustion system for the vehicle or the engine of the vehicle caused by a fuel having excess oxygen from a faulty fuel oxygen conversion unit,
    wherein the control system includes a controller configured to receive the plurality of sensed temperature values, determine the change in temperature of the stripping gas associated with the gas oxygen reduction unit and the change in temperature of the stripping gas associated with the pre-heater, and instruct the control system to generate the maintenance action.

2. The method of claim 1, wherein determining the change in temperature of the stripping gas associated with the gas oxygen reduction unit comprises comparing a distribution of the plurality of sensed temperature values to a known distribution of temperature values along the axial length of the gas oxygen reduction unit.

3. The method of claim 1, wherein the maintenance action indicates the maintenance required is replacement of the gas oxygen reduction unit.

4. The method of claim 1, further comprising, if the stripping gas has not undergone a change in temperature associated with the gas oxygen reduction unit wherein the temperature is below a minimum operational threshold:
    returning to receiving the plurality of sensed temperature values from each temperature sensor of the plurality of temperature sensors associated with the gas oxygen reduction unit.

5. The method of claim 1, wherein each temperature sensor of the plurality of temperature sensors associated with the gas oxygen reduction unit is disposed on a skin of the gas oxygen reduction unit such that each temperature sensor of the plurality of temperature sensors associated with the gas oxygen reduction unit is disposed along an inner surface or an outer surface of the gas oxygen reduction unit.

6. The method of claim 1, wherein each temperature sensor of the plurality of temperature sensors associated with the gas oxygen reduction unit is embedded in the gas oxygen reduction unit such that at least a portion of each temperature sensor protrudes into a flowpath defined through the gas oxygen reduction unit.

7. The method of claim 1, wherein the gas oxygen reduction unit is positioned in a circulation gas flowpath defined from a fuel gas separator to a contactor of the fuel oxygen conversion unit, the gas oxygen reduction unit positioned in the circulation gas flowpath for reducing an oxygen content of a flow of the stripping gas through the circulation gas flowpath.

8. The method of claim 1, wherein the gas oxygen reduction unit is a catalyst.

9. The method of claim 2, wherein the known distribution of the plurality of sensed temperature values associated with the gas oxygen reduction unit is a baseline temperature distribution in which temperature decreases from an inlet temperature sensed by an inlet sensor disposed at the inlet to an outlet temperature sensed by an outlet sensor disposed at the outlet.

10. The method of claim 9, wherein the temperature is below the minimum operational threshold when a highest temperature of the plurality of sensed temperature values associated with the gas oxygen reduction unit is sensed by a temperature sensor of the plurality of temperature sensors disposed at a location past an axial midpoint between the inlet and the outlet such that the highest temperature is closer to the outlet than to the inlet.

11. The method of claim 1, wherein determining the change in temperature of the stripping gas associated with the gas oxygen reduction unit comprises comparing the plurality of sensed temperature values associated with the gas oxygen reduction unit to the minimum operational threshold.

12. The method of claim 11, wherein the minimum operational threshold is a temperature associated with the gas oxygen reduction unit at a given time during operation of the gas oxygen reduction unit, and wherein determining the change in temperature of the stripping gas associated with the gas oxygen reduction unit comprises comparing the plurality of sensed temperature values at the given time to the minimum operational threshold.

13. The method of claim 1, further comprising:
determining, using the plurality of sensed temperature values and a flowrate of the stripping gas through the gas oxygen reduction unit, an amount of oxygen the gas oxygen reduction unit is extracting from the stripping gas.

14. The method of claim 13, wherein the control system is instructed to generate the maintenance action if the change in temperature of the stripping gas associated with the gas oxygen reduction unit is below the minimum operational threshold and the amount of oxygen the gas oxygen reduction unit is extracting from the stripping gas is below an expected quantity of extracted oxygen.

* * * * *